United States Patent [19]
Walton et al.

[11] Patent Number: 5,531,681
[45] Date of Patent: Jul. 2, 1996

[54] APPARATUS FOR ALTERING COMPOSITION OF NUTRITIONAL PRODUCT DURING ENTERAL TUBE FEEDING

[75] Inventors: Joseph E. Walton, Westerville; Terrence B. Mazer, Reynoldsburg; Ronita K. Geckle, Columbus; Carl J. Piontek, Powell, all of Ohio; Susan B. Duel, Laurinburg, N.C.; Andre Daab-Krzykowski, Columbus, Ohio; Mark A. McCamish, Worthington, Ohio; Robert L. Joseph, Columbus, Ohio; William G. Pierson, Canal Winchester, Ohio

[73] Assignee: Abbott Laboratories, Abbott Park, Ill.

[21] Appl. No.: 372,407

[22] Filed: Jan. 13, 1995

[51] Int. Cl.⁶ .................................................. A61M 37/00
[52] U.S. Cl. ........................ 604/83; 604/84; 604/85; 604/8; 604/890.1; 604/892.1
[58] Field of Search ............................ 604/82, 83, 85, 604/56, 403, 405, 408, 409, 410, 415, 416, 251, 254, 255, 256, 257, 258, 260, 262, 890.1, 892.1, 8; 424/422–424, 468–475; 426/540

[56] References Cited

U.S. PATENT DOCUMENTS

| | | | |
|---|---|---|---|
| 4,479,794 | 10/1984 | Urquhart et al. | 604/85 |
| 4,511,353 | 4/1985 | Theeuwes | 604/85 |
| 4,511,551 | 4/1985 | Theeuwes | 604/56 |
| 4,968,507 | 11/1990 | Zentner et al. | 424/465 |
| 4,985,017 | 1/1991 | Theeuwes | 604/92 |
| 5,069,671 | 12/1991 | Theeuwes | 604/251 |
| 5,147,646 | 9/1992 | Graham | 424/424 |
| 5,160,742 | 11/1992 | Mazer et al. | 424/469 |
| 5,162,057 | 11/1992 | Akiyama et al. | 106/243 |
| 5,318,558 | 6/1994 | Linkwitz et al. | 604/892.1 |
| 5,324,280 | 6/1994 | Wong et al. | 604/892.1 |
| 5,385,545 | 1/1995 | Kriesel et al. | 604/82 |
| 5,385,546 | 1/1995 | Kriesel et al. | 604/85 |
| 5,484,410 | 1/1996 | Kriesel et al. | 604/89 |

FOREIGN PATENT DOCUMENTS

WO93/02558   2/1993   WIPO.

OTHER PUBLICATIONS

Potts et al, *Comparison of Blue Dye Visualization and Glucose Oxidase Test Strip Methods for Detecting Pulmonary Aspiration of Enteral Feedings in Intubated Adults*, Chest, vol. 103, Jan. 1993, pp. 117–121.

Nutrition In Critical Care, Gary P. Zolga ed., Mosby-Year Book, Inc., St. Louis, MO (1994), pp. 439–467.

Primary Examiner—Randall L. Green
Assistant Examiner—V. Alexander
Attorney, Agent, or Firm—Brian R. Woodworth

[57] ABSTRACT

An apparatus is disclosed for modifying a liquid enteral nutritional product during delivery thereof from a supply thereof, such as a hangable container, to a feeding tube delivering the liquid enteral nutritional product to the gastrointestinal tract of a patient. The apparatus has at least one formulation chamber, such as a drip chamber, with at least one controlled release dosage form unit in the form of a coated tablet, osmotically driven device, coated capsule, microencapsulated microspheres, agglomerated molecular sieving type material, or a quantity of fine hollow permeable fibers located therein. The controlled release dosage form unit or units contain at least one beneficial agent selected from nutrients, medicaments, probiotics, or diagnostic agents or mixtures thereof, to any of which a physiologically acceptable marker dye in controlled release dosage form and/or the same or different beneficial agent not in controlled release dosage form may be added. A liquid nutritional product flows through the formulation chamber during enteral tube feeding of a patient.

37 Claims, 16 Drawing Sheets

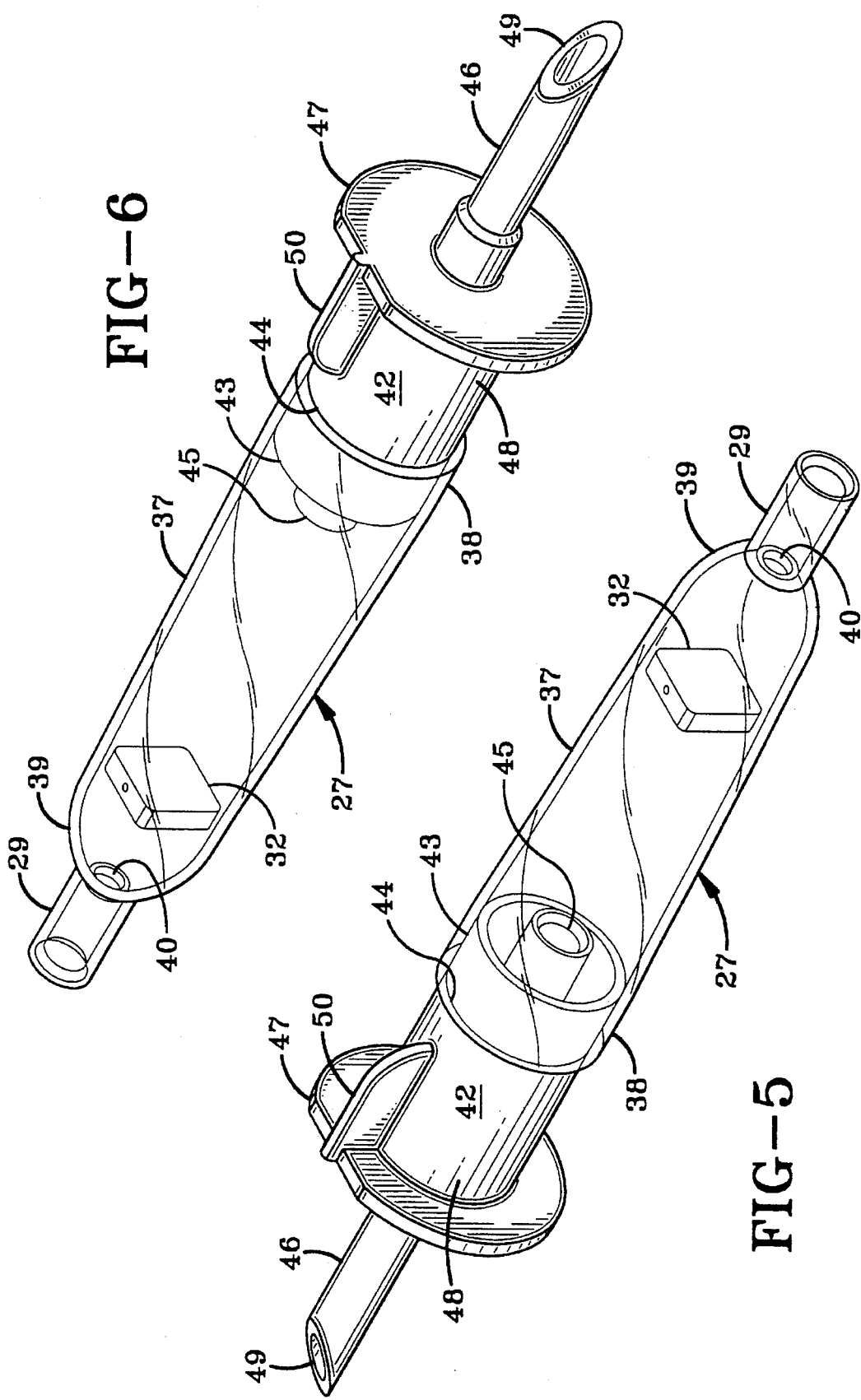

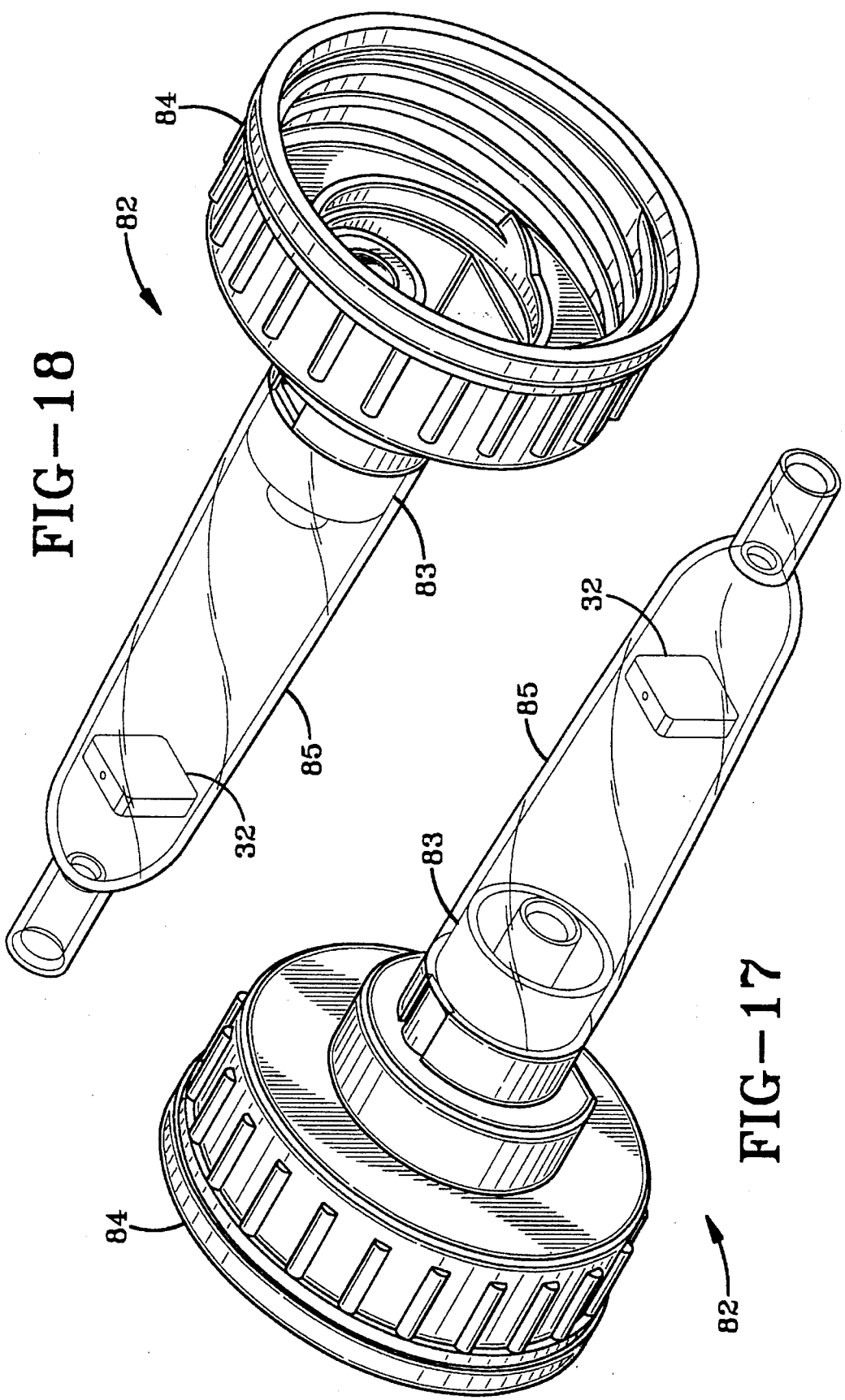

APPARATUS FOR ALTERING COMPOSITION OF NUTRITIONAL PRODUCT DURING ENTERAL TUBE FEEDING

FIELD OF THE INVENTION

The invention relates to an apparatus for feeding liquid enteral nutritional products and particularly to modifying a liquid enteral nutritional product having a viscosity in the range of from 1 to about 300 centipoises (cps.) by adding ingredients during the feeding thereof into the gastrointestinal tract of a patient.

BACKGROUND OF THE INVENTION

The feeding of a liquid enteral nutritional product from a hangable container, such as a bottle or a plastic bag with a bottom outlet connecting to a drip chamber and the latter to a flexible tubing, or lumen, leading to a nasogastric tube or a feeding tube inserted through a gastrostomy or a jejunostomy, by gravity flow or aided by a pump, is well known. The liquid enteral nutritional product may be aseptically processed or terminally retorted, and may be supplied in a pre-filled, ready-to-hang container, or placed in such a container by a caregiver. However, the selection of diets, particularly special diets, from amongst the rather modest number of typically available liquid enteral nutritional products is limited. This narrows, as a practical matter, the choices of the attending physician as to diet modifications, temporary or long term, that might significantly benefit the patient. In view of the now-recognized importance of providing aseptic nutritional compositions, it can be seen that modified diets are not easily prepared without observing the stringent requirements needed to deliver an aseptic nutritional composition to the patient. The need to observe such requirements has heretofore militated against preparing small quantities of special diets designed for a specific patient.

Moreover, a number of nutrients as well as medicaments, diagnostic agents, and other ingredients such as probiotics, that at any given time might be desirable to orally administer to a patient are not stable during heat sterilization or may not be mutually compatible with other desired ingredients for an extended period of time, such as days or even months until used, and thus are not readily amenable to large scale preparation and consequent storage as the product moves through commerce.

Drug delivery systems have been described and claimed in U.S. Pat. Nos. 4,511,353, 5,318,558 and 5,324,280 in which the drug component to be delivered is stored in a capsule from which it is ejected over time upon osmotic infusion of moisture into the capsule, the drug being carried away from the outside surface of the capsule by a suitable liquid in an intravenous, i.e., parenteral, delivery system, or even, by the device of U.S. Pat. No. 5,318,558, by body fluids upon implantation of the capsule.

In U.S. Pat. No. 5,069,671 there is described a formulation chamber, which may also be a drip chamber, in which various forms of sustained release mechanisms are employed to release a drug or medicament, or other physiologically beneficial component such as a nutrient, within the formulation chamber from which the drug or other component is carried by a suitable liquid into a parenteral delivery system.

The teachings of U.S. Pat. Nos. 4,511,353 and 5,069,671 are directed to intravenous delivery of parenteral compositions, and in the case of the latter patent, includes delivery by infusion through intravenous, intraarterial, intraperitoneal or subcutaneous routes. The osmotic dosage system of U.S. Pat. No. 5,324,280 is concerned with the delivery of drug formulations over time to a biological environment, such as a tissue or organ implant in a mammal, or a stream or tank for marine life. The osmotically driven device of U.S. Pat. No. 5,318,558 is said to be usable to deliver drugs, medicaments and nutrients in a range of environments extending from veterinary medicine to human drug administrations, and to hobby situations such as fish tanks. Again, in the case of human administration, the delivery appears to be within a tissue or organ implant.

Although the osmotic delivery devices and other forms of sustained or controlled release dosage forms or reservoirs have been known for some time, so far as is known, there has been no attempt to utilize such a delivery system to add one or more nutrients, or one or more medicaments, or a mixture of nutrients and medicaments, or a probiotic, or a diagnostic agent, or any of these in admixture with a marker dye, to a liquid enteral nutritional product, with a viscosity up to 300 cps., during the administration of the nutritional product to the gastrointestinal tract of a patient. Liquid enteral nutritional products currently on the market are described in the reference text "Nutrition In Critical Care", Gary P. Zaloga, ed., Mosby—Year Book Inc., St. Louis, Mo., 1994, at Chapter 24, authored by Barbara Hopkins, Part III, "Feeding", pp. 439–467. This reference indicates that complete nutrient compositions contain proteins, carbohydrates, fibers, fats, and vitamins and minerals in various proportions in an aqueous or aqueous/fat medium. Nutrient compositions for special diets may omit one or more classes of these components.

SUMMARY OF THE INVENTION

A first aspect of the invention concerns an apparatus for adding ingredients to a liquid enteral nutritional product during delivery of the nutritional product from a supply thereof, such as a hangable container, to a feeding tube delivering the nutritional product to the gastrointestinal tract of a patient.

The apparatus comprises:

a formulation chamber, usually in the form of a drip chamber, connectable to a supply container of a liquid enteral nutritional product, normally an aqueous composition, the formulation chamber having an inlet and an outlet, at least one beneficial agent in controlled release dosage form, each controlled release dosage form unit being disposed in the formulation chamber so as to be wetted by or immersed in the liquid enteral nutritional product traversing the formulation chamber, and each beneficial agent being dispersible in the medium of the liquid enteral nutritional product, and fluid communication means connecting the outlet of the formulation chamber to a tube for feeding the modified enteral nutritional product, containing the so-added at least one beneficial agent, into the gastrointestinal tract of a patient.

Each at least one beneficial agent that is to be added in controlled release dosage form during feeding is added in at least a physiologically effective or diagnostically detectable amount and is selected from the group consisting of: a nutritional ingredient; a medicament ingredient; a chemically and physiologically compatible mixture of: a plurality of nutritional ingredients, or a plurality of medicament ingredients, or at least one nutritional ingredient and at least one medicament ingredient; a probiotic; or a diagnostic agent; and, any of the foregoing ingredients or mixtures of ingredients in admixture with at least one physiologically acceptable, and ingredient compatible, marker dye or dye mixture that is dispersible in the medium of the liquid enteral nutritional product.

The formulation chamber may be a conventional drip chamber which here serves also as the formulation or contact chamber. The formulation chamber may be provided, in addition to the controlled release dosage form or forms therein, and whether or not marker dye is employed, with the same or different beneficial agent or agents not in controlled release dosage form, if desired, in order to add greater amounts of such, or to add a beneficial agent as a bolus. Further, the marker dye or dyes may be provided separately from the beneficial agents, in the formulation chamber, in one or more controlled release dosage forms.

If desired, one or more additional contact or formulation chambers may be employed, either in series or in parallel, but feeding into one fluid communication means leading to the feeding tube of a patient. Wherein more than one formulation chamber is used, at least one formulation chamber will have positioned therein at least one controlled release dosage form containing at least a useful or detectable amount of at least one beneficial agent as above defined, while each additional formulation chamber may contain one or more beneficial agents in either or both controlled release and non-controlled release dosage forms. The use of more than one formulation chamber facilitates the addition of ingredients not readily available in combination or not compatible during storage together in a controlled release dosage form.

In each formulation chamber the beneficial agent or agents, whether in controlled release dosage form or not, are positioned, and held or supported, if necessary, so that the liquid enteral nutritional product being modified contacts and wets or immerses the dosage form of the beneficial agent or agents therein. Preferably, each controlled release dosage form is shaped or held in such a manner as to prevent or avoid the beneficial agent blocking flow of the liquid enteral nutritional product out of the drip chamber or formulation chamber in which it is positioned.

The combination of (1) a formulation chamber, ordinarily in the form of a drip chamber, and (2) fluid communication means, accompanied by (3) at least one beneficial agent, as herein defined, in controlled release dosage form disposed in the formulation chamber, or, merely accompanying the formulation chamber, in either case when the three parts are supplied together, constitutes a useful kit for evacuating a liquid enteral nutritional product from a supply container, such as a hangable container, and modifying the liquid enteral nutritional product by adding one or more beneficial agents thereto as it is flowing from the container and feeding the modified product into the gastrointestinal tract of a patient. The formulation chamber of the kit may also be loaded with or be accompanied by a marker dye or dyes in a separate controlled release dosage form and/or one or more beneficial agents in a suitable non-controlled dosage release form, for example, in uncoated particulate or tablet form in a porous carrier envelope such as a tea bag-like packet. The marker dye or dyes may be of types visible under either or both white light or ultraviolet light. Preferably, the at least one beneficial agent in controlled release dosage form and any other additives in non-controlled release dosage forms supplied as part of a kit are already positioned in the formulation, or drip, chamber. If not, they are readily manually placed in the formulation chamber, ordinarily prior to connecting the apparatus to the supply container from which the liquid enteral nutritional product is to be evacuated.

In a further aspect of the invention, the invention concerns a method of preparing a special liquid diet for enterally feeding a tube fed patient comprising modifying a liquid enteral nutritional product during the flow thereof from a supply container containing such composition to a feeding tube leading into the gastrointestinal tract of the patient. More specifically, the method comprises the steps of:

A. providing an apparatus comprising:
  (a) a formulation chamber having an inlet and an outlet, the inlet being connected in fluid communication to the supply container of the liquid enteral nutritional product,
  (b) a physiologically effective or diagnostically detectable amount of at least one beneficial agent in controlled release dosage form, each beneficial agent being disposed in the formulation chamber so that the dosage form thereof is contacted by or immersed in the liquid enteral nutritional product traversing therethrough, each beneficial agent being dispersible in the medium of the liquid enteral nutritional product and each beneficial agent in controlled release dosage form being selected from the group consisting of: a nutritional ingredient; a medicament ingredient; a chemically and physiologically compatible combination of: a plurality of nutritional ingredients, or a plurality of medicament ingredients, or at least one nutritional ingredient and at least one medicament ingredient; or a probiotic ingredient; or a diagnostic agent; and, any of the foregoing ingredients or combinations of ingredients together with at least one compatible, physiologically acceptable, marker dye that is dispersible in the medium of the liquid enteral nutritional product, and
  (c) fluid communication means capable of operatively connecting the outlet of the formulation chamber to a tube for feeding a liquid enteral nutritional product into the gastrointestinal tract of the patient;

B. providing a supply container containing a liquid enteral nutritional product;

C. placing the apparatus in communicative series in the fluid flow between the supply container and the feeding tube; and, D. flowing the liquid enteral nutritional product through the apparatus wherein the product becomes modified and into the feeding tube.

In a modification of this method which may be especially useful in tailor-making a diet for a patient, one or more beneficial agents that are not in controlled release dosage form are added to the formulation chamber. The added beneficial agent or agents may be the same or different than the specific beneficial agent or agents provided in the formulation chamber in controlled release dosage form. The added beneficial agents which are not in controlled dosage form are added to accomplish a bolus feeding or bolus effect, or, simply to add a greater amount of a given beneficial agent. Also, marker dye in a separate controlled release dosage form, which may be surface coated with readily soluble dye to impart quick initial dye marking, may be added to the formulation chamber. In another modification the fluid communication means is provided with one or more additional formulation, or contact, chambers, that are not necessarily drip chambers, but which each have positioned therein either a marker dye, or, a beneficial agent, as herein defined, in controlled or non-controlled release form, or a combination of marker dye and beneficial agent. The formulation chambers are connected to a supply of liquid enteral nutritional product and positioned so as to permit the flow of the liquid enteral nutritional product over each dosage form therein to contact it or even immerse it dynamically, i.e., immerse it in a quantity of liquid that constantly turns over, in order to take up the beneficial agent and/or dye content and convey such to a feeding tube of a patient. A pump may be used, if needed or desired, to flow or help flow the modified liquid enteral nutritional product into the feeding device or tube.

BRIEF DESCRIPTION OF THE DRAWINGS

The present invention will be better understood with reference to the appended drawings in which:

FIG. 5 is a perspective view of a drip chamber usable according to the invention with a controlled release dosage form in the shape of a substantially rectangular solid with slightly rounded corners disposed within the drip chamber, the beveled inlet tube end of the drip chamber being the upper end that is thrust in the normal manner through the closure of the supply container to communicate therewith and receive liquid enteral nutritional product therefrom;

FIG. 6 is a perspective view of the drip chamber of FIG. 5 inverted to show more of the detail of construction;

FIG. 17 is a perspective view of a suitable formulation chamber similar to that shown in FIG. 5 but with a different form of attachment for connection to a supply container, the cap here is threadably attached to a supply container and is integrally formed with the top of the formulation chamber;

FIG. 18 is a perspective view of the formulation chamber shown in FIG. 17 as viewed in the opposite direction;

DEFINITIONS USED HEREIN

Figure 1:
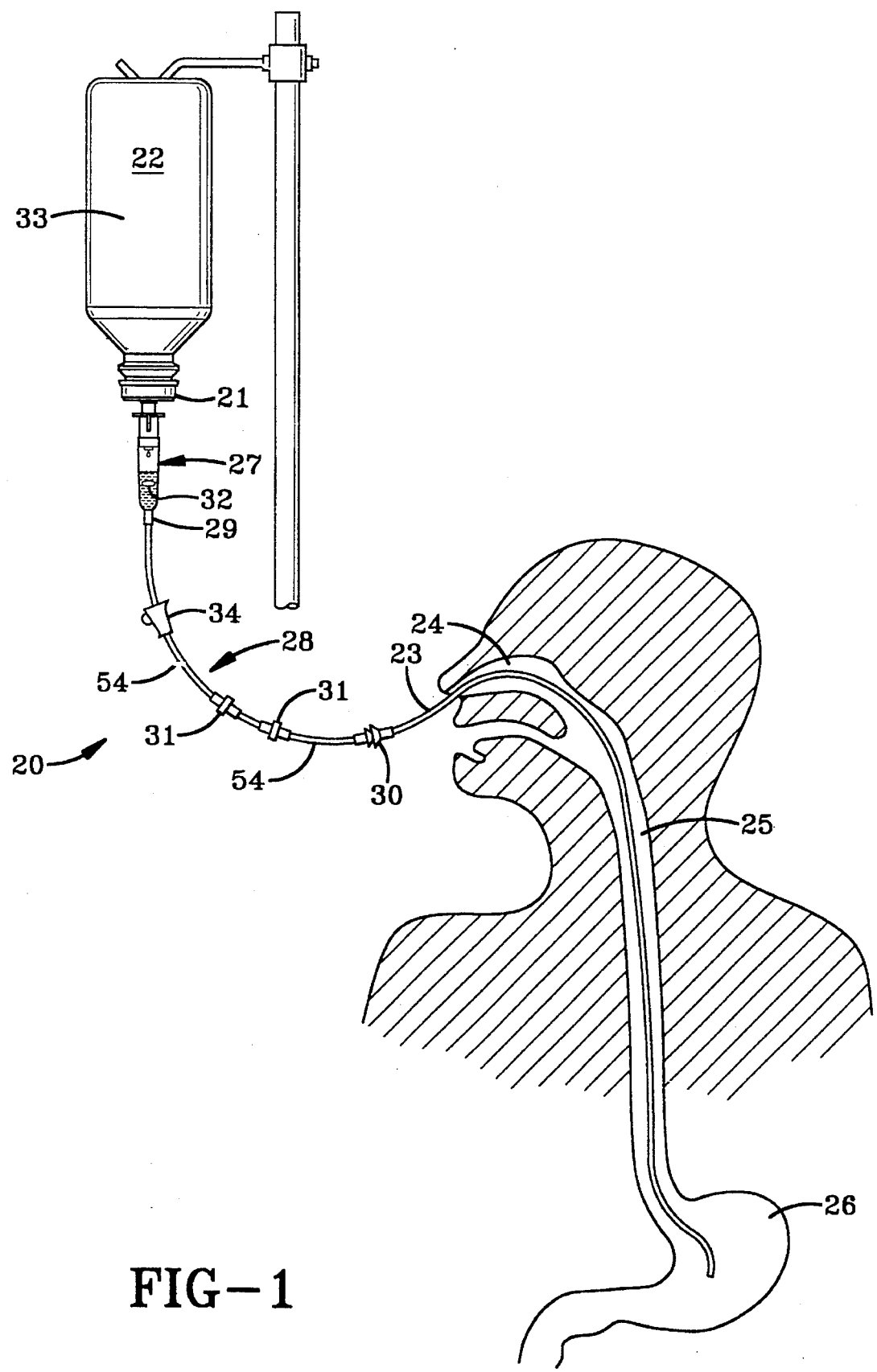
FIG. 1 is a partly schematic representation of an apparatus for modification of a liquid enteral nutritional product and tube feeding it nasogastrically according to the invention.

The following terms and phrases are defined for the purposes of the description and claims.

"Enteral" nutritional products refers to liquid compositions commonly understood to be supplied to and utilized in the gastrointestinal tracts of patients. Such enteral nutritional products have a viscosity in the range of 1 to about 300 cps. and most frequently in the range of about 5 to about 150 cps.

"Enteral nutritional product medium" refers to the liquid portion of a liquid enteral nutritional product, mainly water, but often including lesser or minor amounts of one or more liquid non-aqueous substances such as lipids, e.g., vegetable oil and marine oil.

The term "gastrointestinal tract" as used herein refers only to the stomach and the small bowel. Feeding to the gastrointestinal tract is done by use of a nasogastric tube extending through a nasal passage and the esophagus and thence to the stomach, or by use of a feeding tube extending through the abdominal wall to the stomach or small intestine.

A "physiologically significant" or "beneficial" ingredient is an ingredient that is, or is believed to be, nutritionally or pharmaceutically important to the patient, or is otherwise medically important as in the case of a probiotic, or, a diagnostic agent such as an opaquing agent.

A "probiotic" is understood to be a live microbial food supplement which beneficially affects the human host by improving the individual's microbial balance in the gastrointestinal tract, e.g., *Lactobacillus reuteri*.

A "beneficial agent or ingredient that is dispersible in the medium of the liquid enteral nutritional product" is an agent or ingredient that is physiologically beneficially added, or otherwise usefully beneficially added, as in the case of a diagnostic agent, to the liquid nutritional product during enteral feeding, and is dispersible in the medium of the nutritional product. The beneficial agent(s) or ingredient(s), whether or not supplied by, i.e., from, controlled release dosage form units or devices, and used according to the invention, must be dispersible in the medium of the liquid enteral nutritional product being modified during feeding, in order to be carried along with the nutritional product into the gastrointestinal tract of the patient.

A "useful amount" of a beneficial ingredient that is dispersible in the medium of the liquid enteral nutritional product is an amount that is "physiologically effective or diagnostically detectable" with respect to a patient, i.e., it produces, or is reasonably expected to produce, a detectable beneficial effect on the patient on either a short term or long term basis when fed as part of a liquid enteral nutritional product, or, is detectable in diagnosing a condition or disease. Generally not more than about 5 grams of beneficial agent will be contained in a single controlled release dosage form unit or device, and a plurality or even multiplicity of units such as microencapsulated microspheres containing a given beneficial agent may be employed to provide a desired level of the beneficial agent in the nutritional product being fed.

The phrase "at least one beneficial agent dispersible in the medium of the liquid enteral nutritional product" is meant to refer to the singular as well as the plural, as may well be adjudged from the context, and includes combinations of ingredients, agents or factors.

The term "dispersible" as used herein with respect to beneficial agent(s) or ingredient(s) is to be understood to apply to substances that are soluble as well as those that are suspendable enough to be taken up readily and carried along by the liquid medium as the liquid enteral nutritional product flows through the formulation chamber containing the one or more controlled release dosage forms.

The term "feeding set" refers to the combination of a drip chamber, or other formulation chamber, and fluid communication means leading to a feeding tube for enteral feeding. The drip chamber or other formulation chamber is loaded with or accompanied by at least a useful amount of at least one beneficial agent in controlled release dosage form, the beneficial agent being as above defined with or without a marker dye in combination and with or without additional beneficial agent that is not in controlled release dosage form. The term also encompasses such a feeding set having at least one additional drip chamber or one or more formulation chambers in fluid flow series or in parallel, as a part of the fluid communication means, each feeding set having at least one drip chamber or formulation chamber loaded with at least one beneficial agent in controlled release dosage form, each beneficial agent being present in at least a useful amount as above defined. Where more than one formulation chamber is employed, the additional chamber or chambers may contain: (1) one or more beneficial agents in controlled release dosage form only, with or without marker dye in controlled release dosage form; or (2) one or more beneficial agents in controlled release dosage form intermingled with one or more beneficial agents not in controlled release dosage form, and with or without marker dye in controlled release dosage form; or (3) one or more beneficial agents none of which are in controlled release dosage form, and with or without marker dye in controlled release dosage form.

The process of "infusion" is meant to refer, in the present context, to the process of supplying an enteral-soluble beneficial ingredient to the gastrointestinal tract of a patient extending over time from at least a minute to about 30 hours, but more usually at least about 2 hours to about 24 hours.

The term "delivery means" denotes generically a means or system for storing and subsequently delivering or releasing a beneficial ingredient or agent or mixture thereof within a formulation chamber such as a drip chamber during, and as a consequence of, the flow therethrough of a liquid enteral nutritional product utilizing a controlled release dosage form of the beneficial ingredient or agent.

The term "a controlled release dosage form" refers to any of the well known conventional controlled release forms, such as a coated tablet, osmotic delivery device, coated capsule, microencapsulated particles such as microspheres, agglomerated particles, e.g., molecular sieve particles, or a fine, hollow, permeable-walled fiber as a bundle of chopped fibers or a coil, each a form that contains and stores and subsequently releases, or disperses in the case of the osmotically driven devices, a useful content of a beneficial agent into the medium of a liquid enteral nutritional product at room temperature in a slow, or delayed or intermittent manner as compared to the solubility characteristics normally exhibited by that beneficial agent, when in uncoated or untreated particulate form, in the said medium at about room temperature. Any dosage form which employs coating, encapsulation, microencapsulation, enclosure in an osmotically driven device, or capture in a molecular sieving type structure or in a permeable fine hollow fiber, to retard or slow down, delay or intermittently delay solubilization of a promptly soluble beneficial agent so that its dissolution, or disperson as with an osmotically driven device, takes place during the course of at least 30 minutes, and preferably at least two hours, of contact by flowing liquid enteral nutritional product, or, the release is delayed, i.e., not commenced, for at least 10 minutes after initial contact in a formulation chamber by the liquid enteral nutritional product, is exhibiting controlled release behavior. As to a beneficial agent that is inherently not promptly soluble in the medium of a liquid enteral nutritional product, any such dosage forms that retard or slow down, delay or intermittently delay solubilization of such a beneficial agent by at least 20 percent of the normal time for solubilization or dispersion into the medium of a liquid enteral nutritional product, of a given unit amount of the beneficial agent that is not coated or treated to obtain a controlled release is considered for the purposes of the description and claims to be a controlled release dosage form. Preferably, the controlled release dosage forms prolong release of the contents thereof for a time appropriate to the nutrient or medicament or other beneficial agent being supplied.

On the other hand, merely tableting a beneficial agent either unmixed with another material, or not admixed with a relatively insoluble binder type excipient, for example, while resulting in a smaller surface area being exposed to a solvent liquid and a slower dissolution rate than that of a fine particulate form of the beneficial agent, is not to be considered making the beneficial agent into a controlled release dosage form. Clearly, a beneficial agent in a particulate form that has not been coated with or enclosed in any other material is not in controlled release dosage form. Nor are uncoated tablets or particles of a beneficial agent, clearly not in controlled release dosage form, to be considered transformed into controlled release form merely by being enclosed in a carrier such as a fibrous tea bag type of packet or an easily dissolved or disintegrated capsule.

The "controlled release dosage forms" useful according to the invention are understood to include delayed or intermittent release as well as sustained release dosage forms, some of which constitute "rate controlling means" or "rate controlled dosage forms". Preferably, the controlled release dosage forms prolong release of the contents thereof for a time appropriate to the nutrient or medicament being supplied.

The terms "controlled release dosage form units" or "controlled release dosage form particles" are to be understood to refer to individual coated tablets or coated capsules or devices such as osmotic delivery devices or microcapsule particles or small bundles of fine hollow fibers or small agglomerated clumps of molecular sieving type material, each capable of the sustained delivery or delayed or intermittent delivery of beneficial agent or marker dye as defined above.

It should also be understood that the phrase "flowing the liquid enteral nutritional product through the apparatus, wherein it becomes modified, and into the feeding tube" is meant to include utilizing gravity flow from a hanging container, as well as using a pump in addition to or without gravity flow to promote the flow of the modified liquid enteral nutritional product into and through a feeding tube.

DETAILED DESCRIPTION OF THE INVENTION

Referring now to the drawings in which like parts are referred to by like reference numerals, the apparatus of the invention is shown in FIG. 1 in the form of a feeding set, indicated generally by the numeral 20, connecting the outlet 21 of the hanging supply container 22 to the nasogastric feeding tube 23 that extends through a nasal passage 24 of the patient and down the esophagus 25 to the stomach 26. The feeding set here consists of a formulation chamber 27, in the form of a drip chamber that serves also as a contact or formulation chamber, and fluid communication means indicated generally by the numeral 28.

Figure 16:
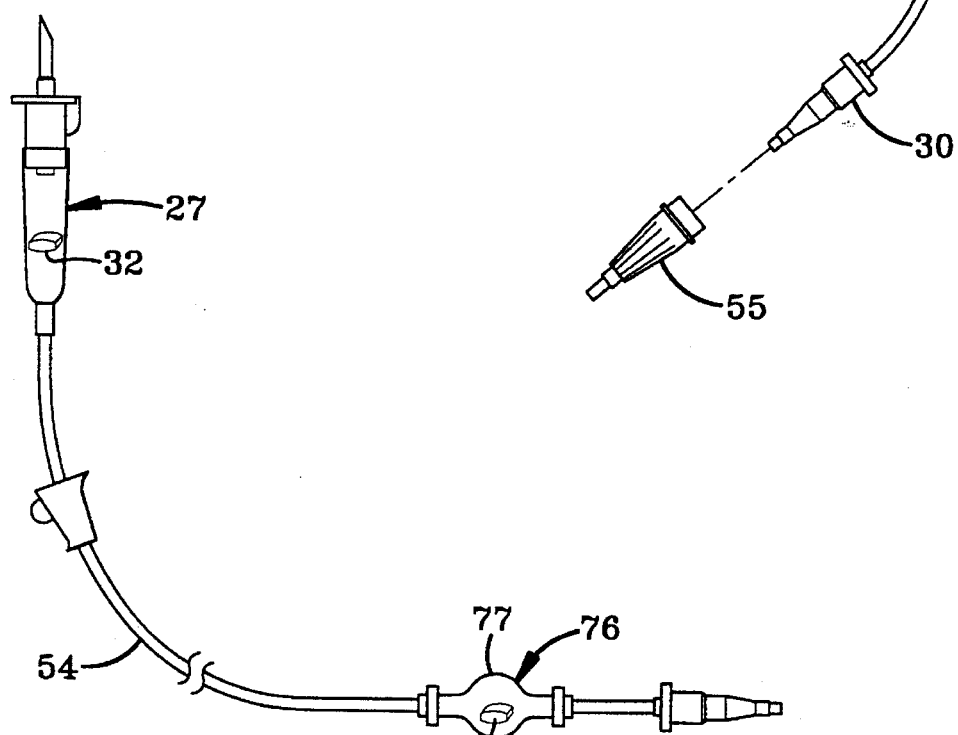
FIG. 16 is a view in side elevation of a feeding kit in which a second formulation chamber has been attached by its inlet in fluid communication to the end of the flexible tubing that normally attaches to a fitting that connects to the feeding tube of the patient, the outlet tube of the formulation chamber having a fitting for connection to the feeding tube.
Figure 19:
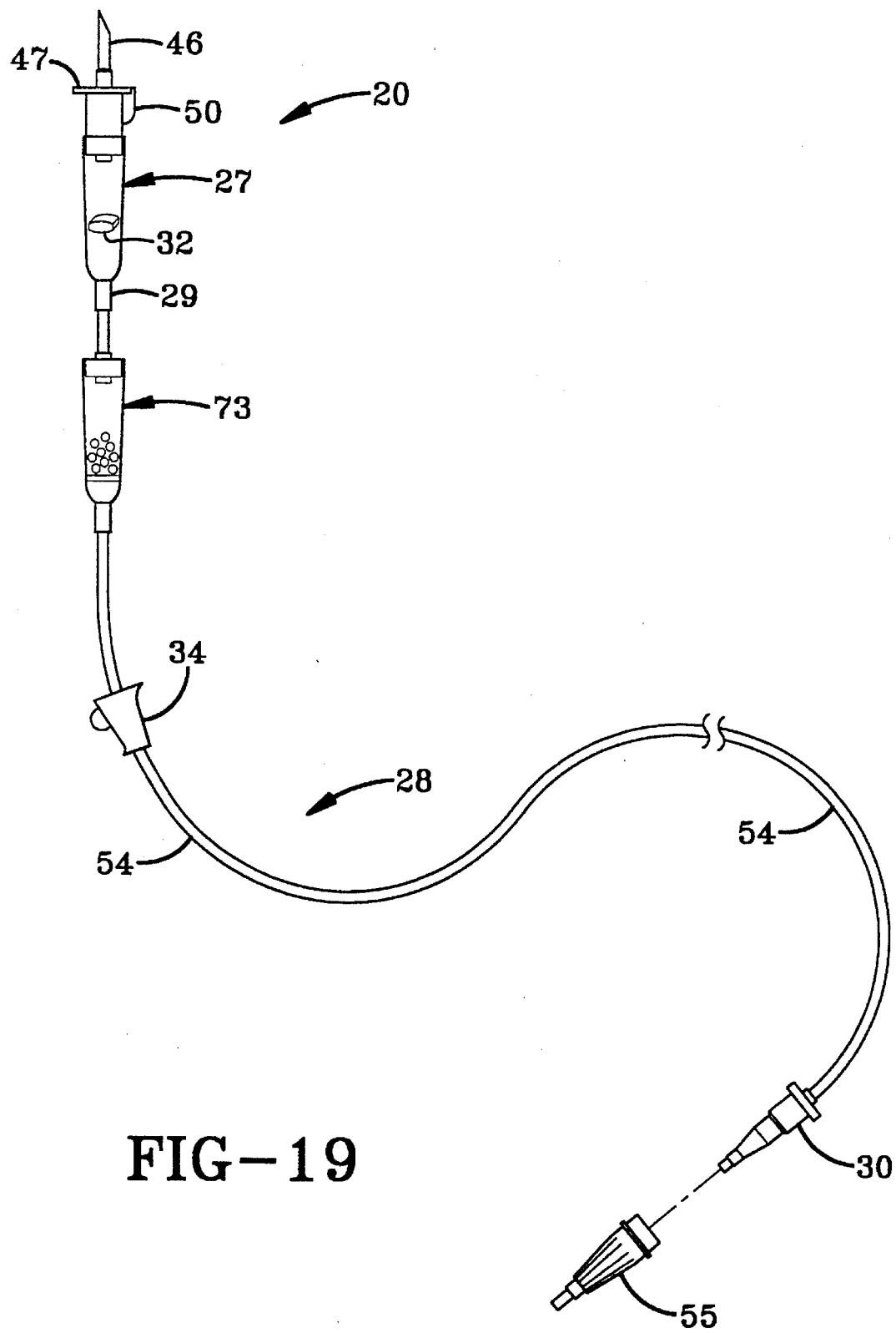
FIG. 19 is a side elevation of a feeding set in which two formulation chambers are connected in series, here in tandem.
Figure 20:
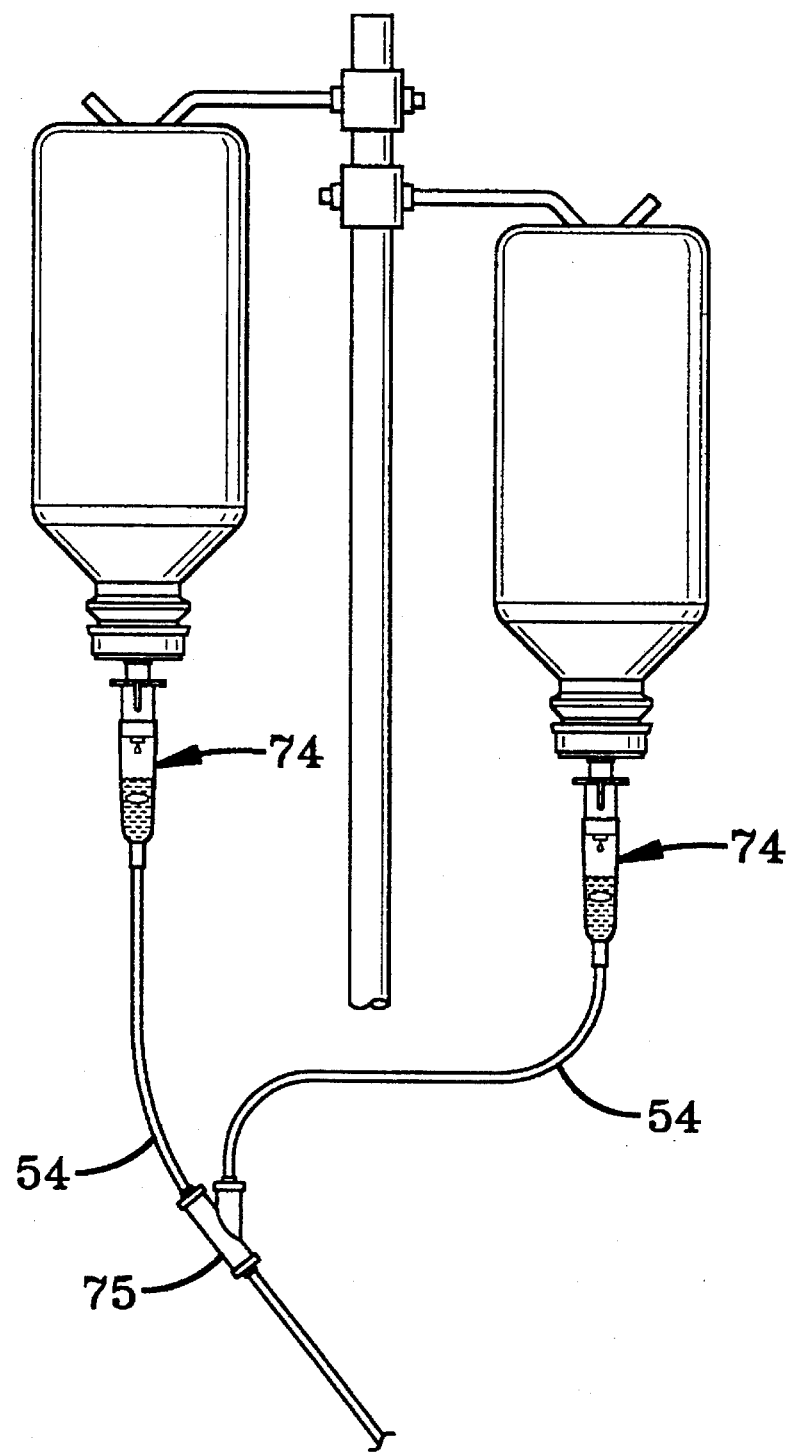
FIG. 20 is a view in side elevation of part of the apparatus for modifying a liquid enteral nutritional product during enteral feeding wherein two formulation chambers are suspended from respective hanging supply containers, each containing liquid enteral nutritional product, the outlets of the formulation chambers being connected to tubing segments that connect to a "Y" fitting that joins the parallel flow from each formulation chamber into a single stream within the communication means, here truncated.

"Fluid communication means" is to be understood to include all components of fluid communication utilized in series from the drip chamber outlet 29 to the connection 30 to the feeding tube, such as the nasogastric feeding tube 23. Components include not only portions of flexible tubing 54 but also any additional drip chambers or other formulation chambers connected in series as seen in FIGS. 16 and 19 for series flow, or in parallel but soon joined into a single stream as seen in FIG. 20, for flow of the liquid enteral nutritional product to the feeding tube of the patient. The components may also include any special tubing portions needed for utilization of a pump, and, connector elements, respectively, between all the other components, such as connector elements 31 or adapters 30.

It may be helpful to utilize two formulation chambers in tandem, such as drip chambers 27 and 73 as seen in FIG. 19, to introduce a greater concentration or amount of a given ingredient. The formulation chambers may be used in tandem also to introduce different respective beneficial ingredients that are not supplied together within the same controlled release dosage form unit or particle. The respective ingredients may constitute a little-used combination, for example, or they may not be compatible in storage together within a controlled release reservoir.

Two formulation chambers are shown in use sequentially in series in the feeding set of FIG. 16 wherein the second formulation chamber 76 is attached at the end of the flexible tubing 54 which is distal from the supply container. This may be found useful for adding a special beneficial ingredient to a feeding set already made up. With the formulation chamber 76 at the end of the set which is distal from the supply container, it will most likely be positioned horizontally as depicted, and is preferably made with a bulbous mid-portion 77 or a low lying longitudinal channel portion wherein the beneficial agent 32 in controlled release dosage form will lie at the lower side of the formulation chamber and be wetted by the flowing liquid enteral nutritional product. If the beneficial agent is not in controlled dosage form it will likewise lie, for example, at the lower side of the bulbous section 77 until dispersed.

Dual formulation chambers 74 may be used in parallel as indicated in FIG. 20, and for the same reason as the tandem chambers, or, it may be simpler wherein it is desired to feed one beneficial agent on a bolus basis and another on a sustained basis. It is preferable to hang such chambers from respective supply containers, as shown, to avoid problems of control in order to get adequate flow through both formulation chambers from a single supply container, which would preferably require the use of a splitter valve to apportion intake flow between the two parallel routes. The outlets of each formulation chamber shown in FIG. 20 are connected to segments of flexible tubing 54 that lead to a "Y" fitting 75 in which the streams of liquid enteral nutritional product are joined.

Referring again to FIG. 1, the formulation chamber 27 has positioned therein a controlled release dosage form unit 32 containing at least a physiologically effective or diagnostically detectable amount of at least one beneficial ingredient that is dispersible in the medium of the liquid enteral nutritional product 33 flowing from the supply container 22 into the formulation chamber 27 where the liquid enteral nutritional product, which is normally water-based, contacts the controlled release dosage form unit 32, wetting it or immersing it within the formulation chamber 27, causing the release or discharge into the nutritional composition of the dispersible beneficial ingredient or ingredients, in addition to marker dye if included, stored in the reservoir. The flow of liquid enteral nutritional product is conveniently started or shut off or sometimes regulated by the use of a conventional adjustable compression clip 34.

Figure 2:
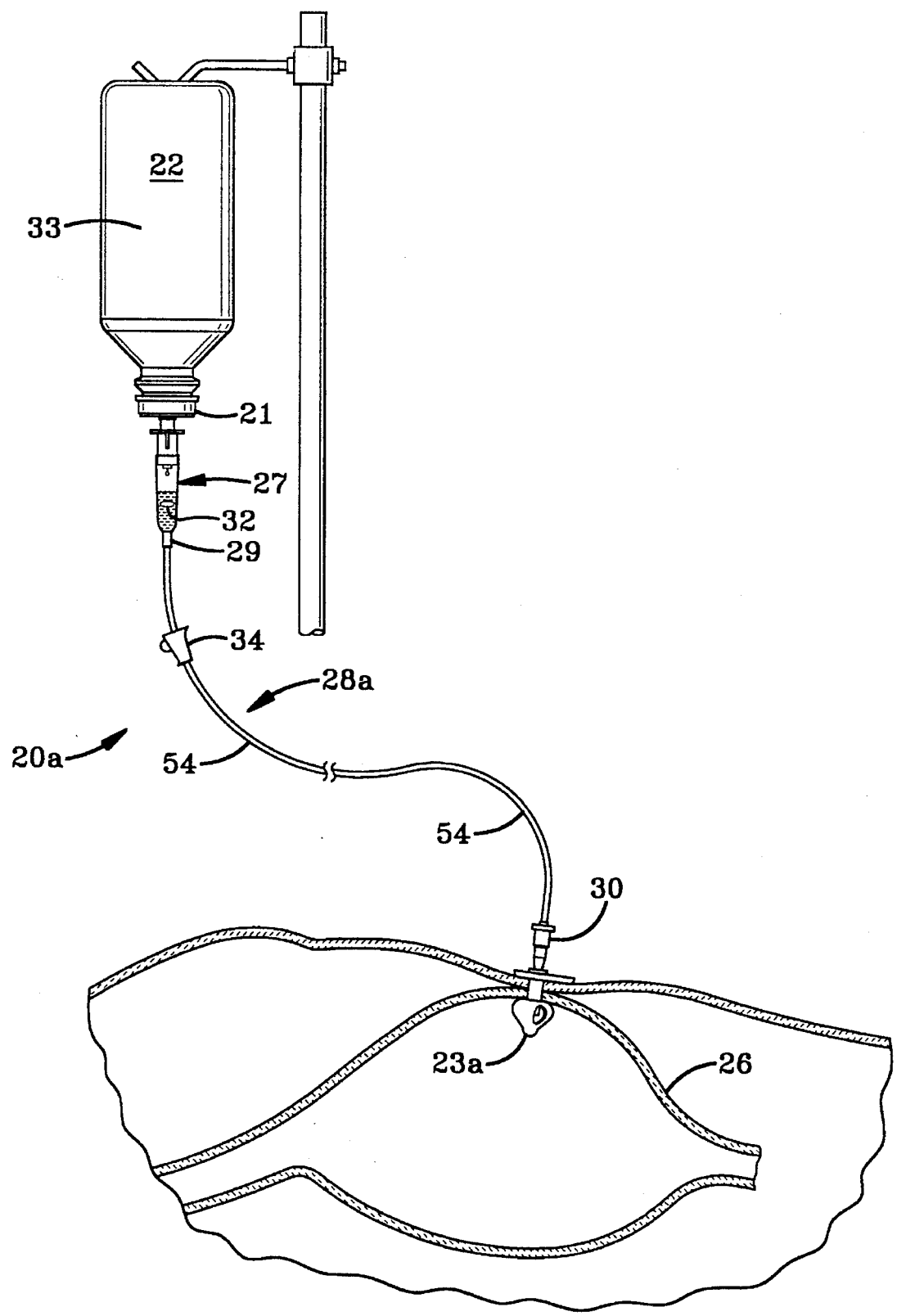
FIG. 2 is a partly schematic representation of an apparatus for modification of a liquid enteral nutritional product and tube feeding it via a gastrostomy tube according to the invention.

Turning now to FIG. 2, a hanging supply container 22 is shown supplying liquid enteral nutritional product 33 to a formulation chamber 27 from which the liquid enteral nutritional product flows through flexible tubing 54 of the feeding set 20a to the gastrostomy feeding tube 23a. The gastrostomy feeding tube shown in FIG. 3 is merely exemplary of the large variety of gastrostomy feeding tubes which are commercially available, it being understood that the apparatus of the present invention is usable with a variety of gastrostomy feeding tubes.

Figure 3:
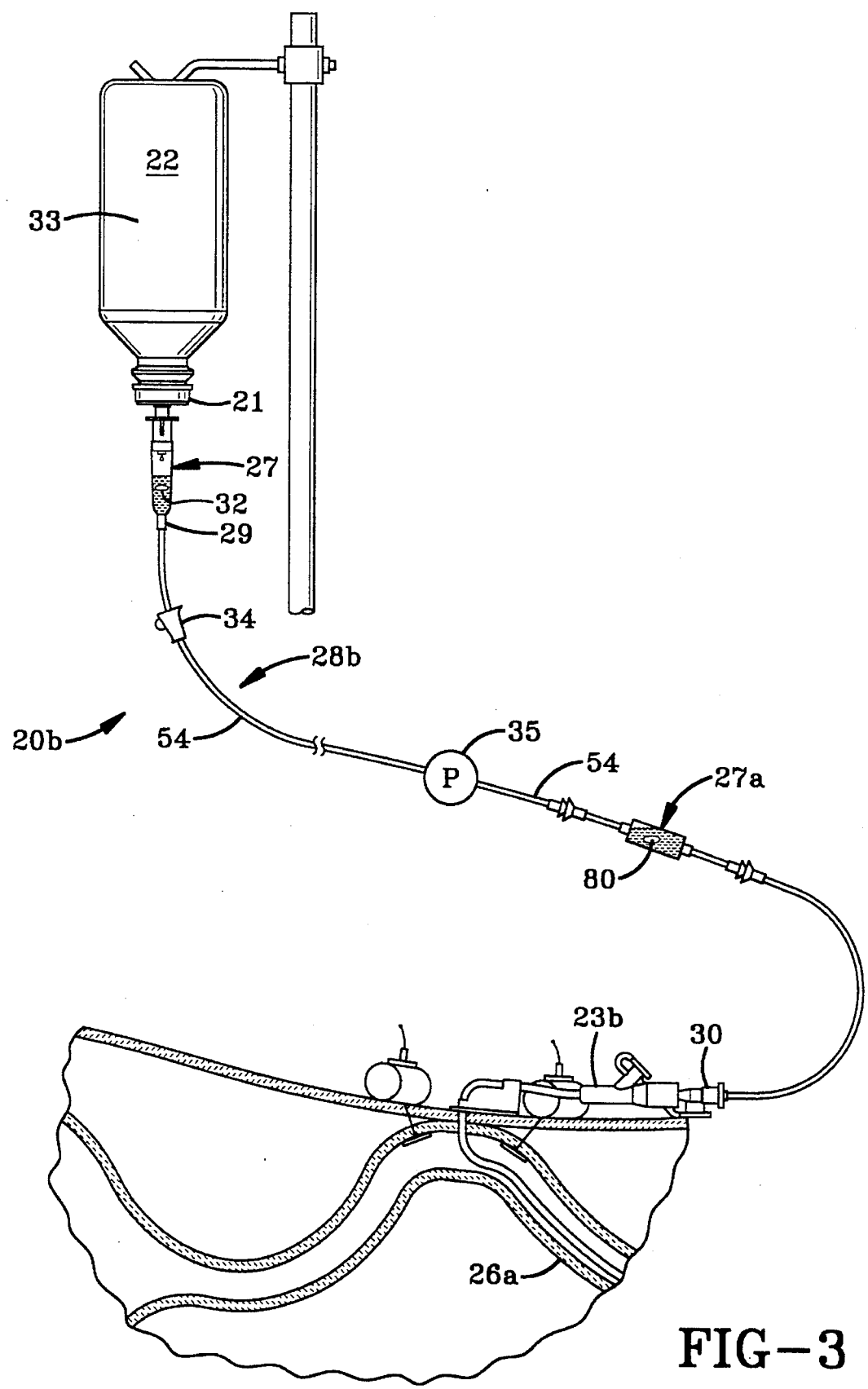
FIG. 3 is a partly schematic representation of an apparatus for modification of a liquid enteral nutritional product and tube feeding it, with the aid of a pump, via a jejunostomy tube according to the invention.

In FIG. 3 there is shown a feeding arrangement for a jejunostomy much like the apparatus in FIG. 1, except that the feeding set 20b is adapted to be used with a pump 35 which provides positive flow into a feeding tube 23b leading to the small bowel 26a of the patient, whereas in a number of cases gravity flow is utilized. Also, a second formulation chamber 27a is employed as part of the feeding set 20b in order to add additional or different beneficial agent and/or marker dye, each dispersible in the medium of the liquid enteral nutritional product 33 flowing from the supply container 22 to formulation chamber 27 and thence through the rest of the communication means 28b and formulation chamber 27a of feeding set 20b to the jejunostomy feeding tube 23b. The additional beneficial agent may be in controlled or noncontrolled dosage form.

If desired, or needed, as often is the case when feeding via a feeding tube, such as a jejunostomy tube, a pump, such as a peristaltic pump with cam action acting upon the flexible tube portion 54 of the communication means 28, or a positive displacement pump with a disposable fluid infusion pumping chamber cassette such as that described in U.S. Pat. No. 4,927,411, and connected in series in the communication means, may be used to flow or help flow the modified liquid enteral nutritional product into the feeding tube, for example, when it is not convenient to hang or otherwise locate the supply container in an elevated position relative to the patient, or, when the nutritional product is rather viscous and flows slowly by gravity flow. The fluid communication means 28 of the apparatus utilized will ordinarily include a flexible tubing portion 54 connectable to or usable with a conventional pump. If the pump employed, for example, is a peristaltic pump that requires especially shaped flexible tubing, such tubing may be substituted for all or a part of the communication means delivering modified nutritional product from the formulation chamber to the feeding tube of the patient.

Figure 15:
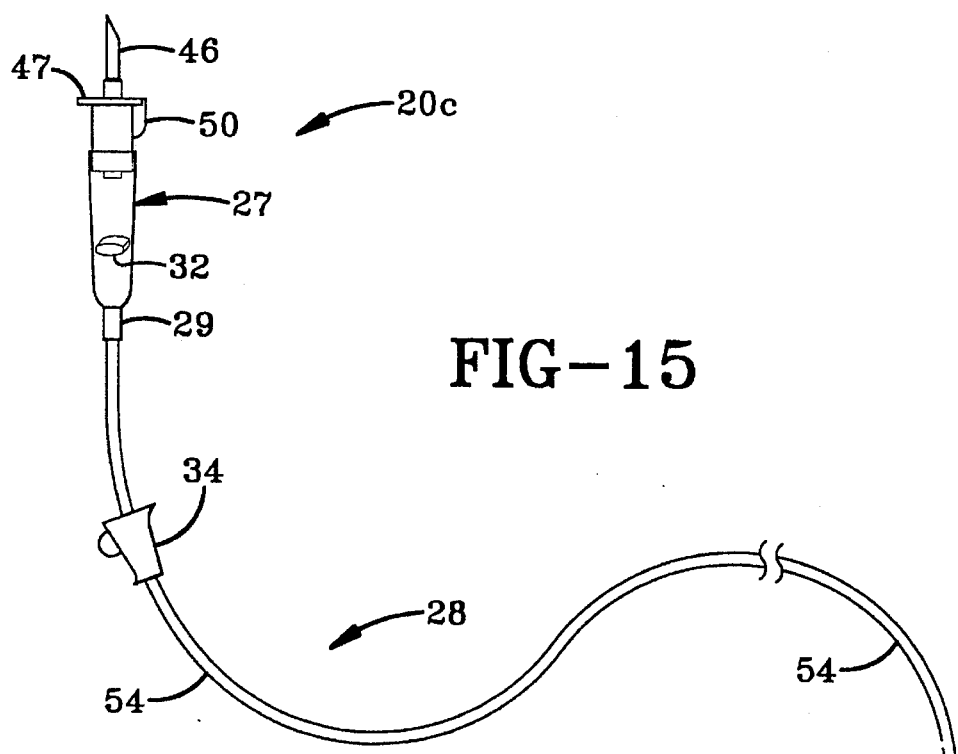
FIG. 15 is a side elevation of a feeding set according to the invention, including a drip chamber, loaded with a beneficial agent in controlled release dosage form, and fluid communication means to connect the drip chamber with the feeding tube used to direct the modified liquid enteral nutritional product to the gastrointestinal tract of a patient, including a protective removable cap for the end connector.

The end of the flexible tubing 54 connected to the inlet end of second formulation chamber 27a is preferably provided with a coupling element 30 such as that shown in the feeding set in FIG. 15, while the inlet end of the formulation chamber is shaped complementarily to receive the coupling element, and the outlet of the formulation chamber communicates with a short length of flexible tubing which likewise terminates in a coupling element 30, that is connected to the feeding tube 23b. It may be seen that it is convenient to add the second formulation chamber 27a, when the need arises, without having to disconnect the parts of the feeding set. Here, for example, the flexible tubing 54 would have to be disconnected from the drip chamber 27 to add the formulation chamber 27a directly in tandem at that end of the set.

Figure 14:
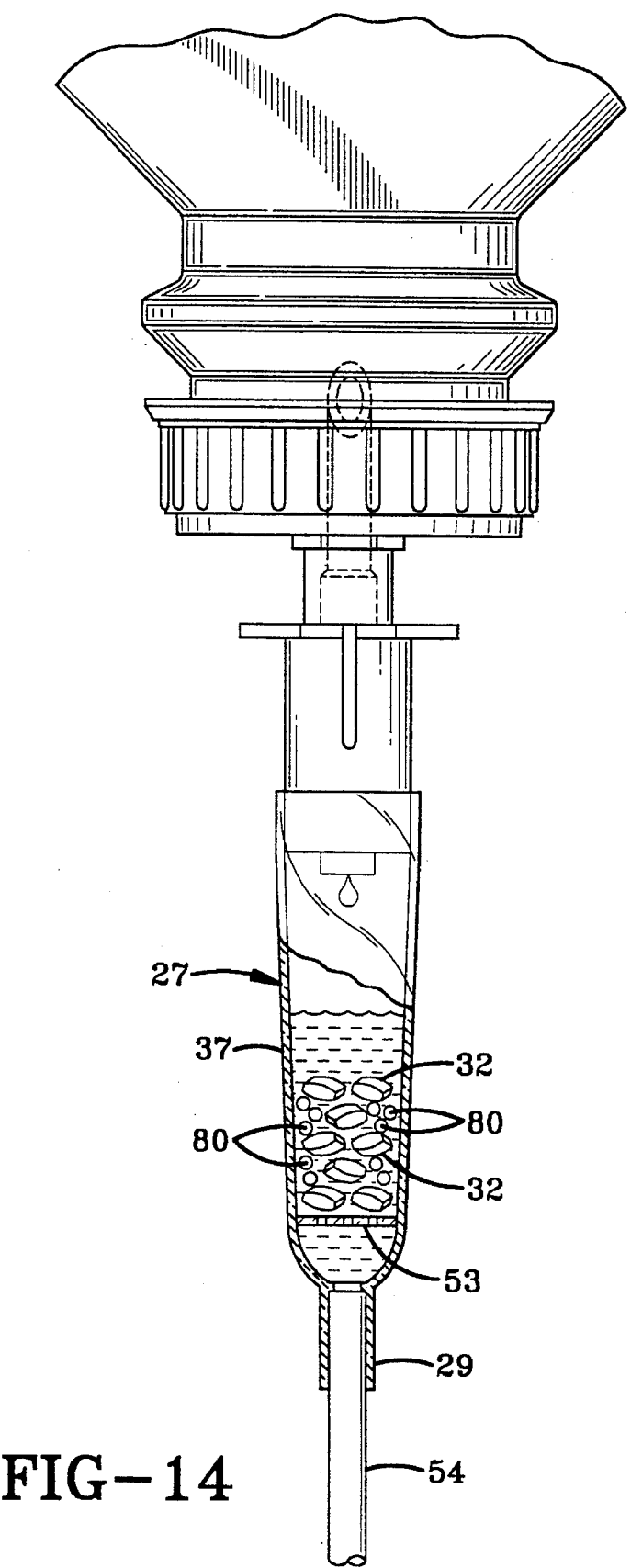
FIG. 14 is a view in side elevation similar to FIG. 13 showing a drip chamber depending from a supply container with liquid enteral nutritional product flowing through the chamber over a beneficial agent in a controlled release dosage form intermingled with added beneficial agent not in controlled dosage form while the dosage forms are supported on a perforated plate near the bottom of the formulation chamber.

The formulation chamber 27 has been loaded with a beneficial agent in controlled release dosage form 32, while the second formulation chamber 27a has been provided with the same or a different beneficial agent not in controlled release dosage form. The use of beneficial agent not in controlled release dosage form is illustrated also in FIG. 14 where a plurality of sustained release dosage form units 32 containing beneficial agent(s) are supported above the pierced plate 53 along with beneficial agent not in controlled release dosage form as particles or dispersible tablets 80.

The formulation chamber 27a may be hung vertically, like a conventional drip chamber, but will probably be more conveniently positioned with the direction of flow of the liquid enteral nutritional product therethrough approximately horizontal. Consequently, the formulation chamber 27a should be provided with means to guide or channel the liquid nutritional product to physically contact the controlled release dosage form unit or units therein. Such means may be a low lying longitudinal channel in the body wall or a bulbous enlargement of the chamber body of the sort illustrated in FIG. 16 or even a simple lateral depression in the sidewall of the lower side of the chamber, or, a trap, or weir, or any other means to retain the dosage form units where there will be an adequate flow or depth of liquid sufficient to afford good contact with the controlled release dosage form units or particles located in such guide or channel means. As seen in FIG. 16, a feeding kit has been provided with a second formulation chamber 76 with a bulbous body portion 77 in which a controlled release dosage form unit 32 is positioned so that flow of liquid enteral nutritional product will steadily contact the controlled release dosage form unit 32 and take up beneficial agent therefrom.

Figure 4:
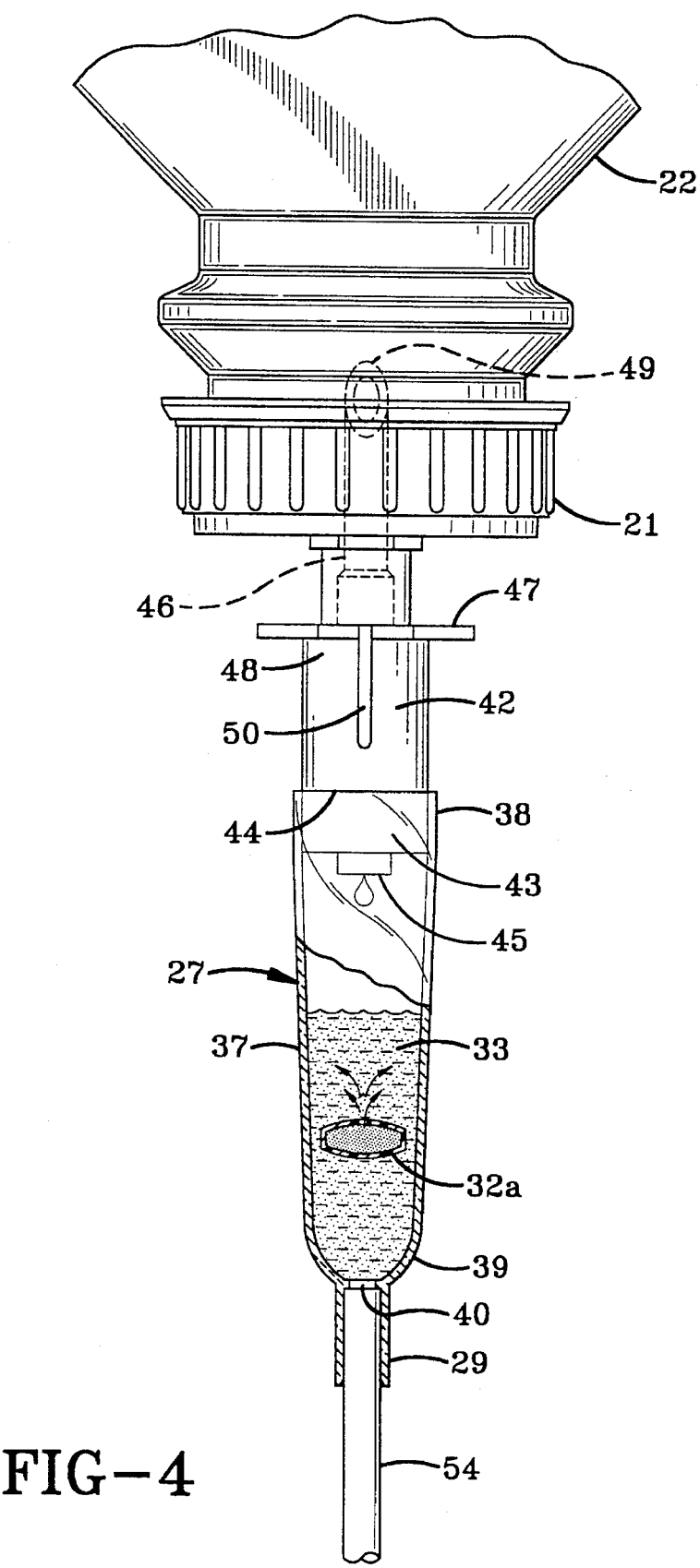
FIG. 4 is an enlarged fragmentary view in front elevation of the lower portion of a hanging supply container of a liquid enteral nutritional product, such as the container shown in FIGS. 1 to 3, with the beveled inlet tube of a drip chamber inserted through the closure and depending therefrom and with a beneficial agent in controlled release dosage form disposed inside the drip chamber and immersed in the flowing liquid enteral nutritional product, the lower part of the drip chamber and the controlled release dosage form within being partly broken away and in section, and the tubing portion of the fluid communicating means, i.e., primarily the tubing leading away from the drip chamber, being truncated for purposes of illustration.

In the enlarged fragmentary view in FIG. 4, a controlled release dosage form unit 32a in the form of an osmotic device capsule is seen immersed in a liquid enteral nutritional composition 33 within the drip chamber 27. This kind of controlled release dosage form unit 32a, which has an outer coating or membrane that does not disintegrate readily, should have, preferably, a geometric shape, for example, that of a rectangular solid, that will avoid blocking flow of liquid enteral nutritional product 33 through a circular opening such as that of the channel 40 serving as the outlet of the lower part 39 of the drip chamber 27, or, other means such as a mesh sleeve may be employed to prevent such blockage.

The details of construction of one example of a conventional drip chamber suitable for use as a formulation chamber according to the invention are illustrated in FIGS. 5 and 6 which are greatly enlarged perspective views. The drip chamber 27 as shown has two parts. The first part is a hollow, nearly cylindrical chamber body 37 with an open first end 38, which is the upper end when the drip chamber is in its normal operative position, and a second end 39, opposite the first end, that tapers or narrows down to form an orifice 40 leading to an integrally formed outlet tube portion 29. The chamber body 37 is preferably formed of a clear material, such as plastic or glass, to allow see-through visibility of the flow of the nutritional product. Usually the drip chamber is formed of a clear, somewhat flexible, autoclaveable plastic, such as a clear polyvinylchloride or polyolefin resin.

The second part of the drip chamber 27 shown is in the nature of a plug 42 with a cylindrical body that has an inward end portion 43 that snugly press fits into the inlet end 38 of the chamber body 37. Preferably the end portion 43 of the plug body 37 that extends into the chamber body has a slightly reduced diameter. The edge 44, of this end portion 43, remote from the end face of the plug is raised slightly, being a little larger in diameter, and serves as a stop when assembling the chamber body and the plug together. The plug body is provided with an integrally formed fluid communication passage 45 which may take the form of an axial borehole in a solid plug body that communicates with an inlet tube portion 46 that projects outwardly in the axial direction from a collar-like flange 47 that extends radially from the top end 48 of the plug body. But, preferably, in order to provide a plug body with more resiliency for easier insertion into the upper end 38 of the chamber body 37, the fluid communication passage 45 is a concentric tube axially located within and about as long as the plug body. The concentric tube 45 is integrally formed with or otherwise operatively connected to the inlet tube portion 46. A short, peripheral, integrally formed flange 50 that extends longitudinally from the collar-like flange 47 along a side of the plug body may be provided, if desired, to aid in gripping the plug body when assembling the drip chamber.

The plug may be molded of a plastic such as a polyvinylchloride resin, which may be pigmented, if desired, for visibility as an aid to observe proper seating in the chamber body.

The distal or free end 49 of the inlet tube portion 46 has a sufficiently sharp beveled end to facilitate puncturing the seal (not shown) in the closure 21 in the neck of a conventional hanging supply container, such as supply container 22. The collar-like flange 47 serves as a stop to the insertion of the pointed inlet tube portion 46 into the closure 21 at the neck of the supply container 22.

Other modes of construction of the formulation chamber may be employed so long as a suitable connection to the supply container is provided as well as a see-through tubular portion wherein the rate of flow of the liquid enteral nutritional product may be observed. For example, see the formulation chamber 82 depicted in FIGS. 17 and 18 wherein the plug end 83 of the formulation chamber is integrally formed with the closure 84 for a conventional supply container to be threadably connected thereto. The apparatus of the invention is not to be considered limited to the inclusion of any of the drip chambers here used by way of illustration, nor is the method limited to the use thereof.

The drip chamber shown in FIGS. 5 and 6 has a controlled release dosage form unit 32 disposed therein ready for use. The controlled release dosage form unit will be preselected according to the contents thereof to provide the additional nutrient(s) and/or medicament(s) and/or probiotic(s) and/or diagnostic agent(s) and/or other beneficial ingredient(s) selected by the care giver in charge, along with a marker dye, if desired. As used herein and in the claims, medicaments are understood to be substances used in therapy. The formulation chamber, or chambers, selected may contain more than one controlled release reservoir in order to provide a combination of nutrients, or, a combination, such as nutrients and medicaments or other beneficial agents, tailored to the needs of the patient being fed. The formulation chamber may also be one provided with the same or different beneficial agent or agents both in controlled and not-controlled release dosage form in order to provide, for example, a greater amount, as in the case of a nutrient. A non-controlled dosage form of a beneficial agent may be used to supply the beneficial agent over a shorter period of time, as might be desired with a medicament.

Figure 11:
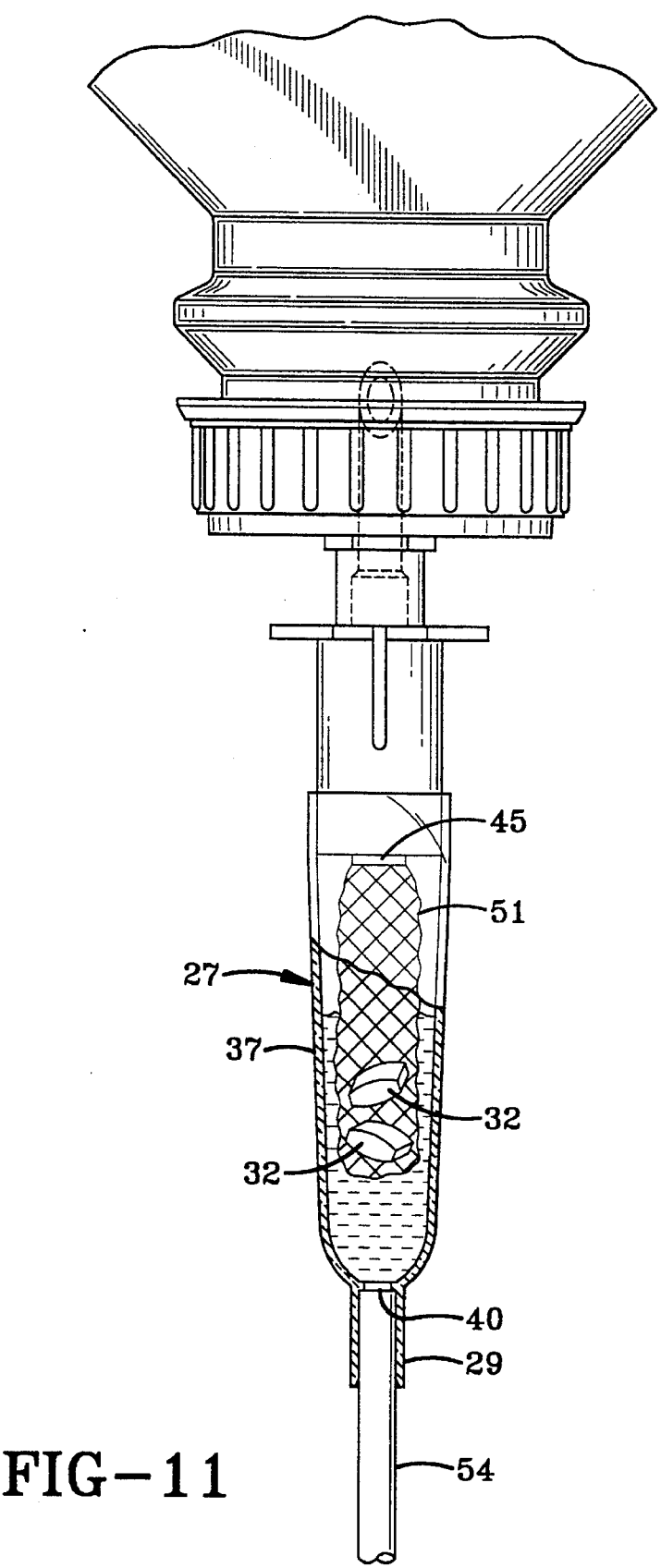
FIG. 11 is a view similar to FIG. 4, but with the controlled release dosage forms of any of FIGS. 7 to 9A confined within a mesh sleeve or bag.

The controlled release dosage form units employed will preferably be in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. To avoid having a dosage form unit or particle block the flow of the liquid enteral nutritional composition through the outlet orifice 40 of the drip chamber, if the dosage form unit is one that maintains integrity of the exterior layer or coating thereof while the ingredients leach out or are expressed out during contact with the liquid enteral nutritional product, it is preferred that the dosage form unit have a geometric shape, e.g., a rectangular solid, or a star shape, either of which will not fully block a round passageway. If a different type of controlled release dosage form is used which dissolves or disintegrates so the interim shape is not controllable, or if it leaves an insoluble skeletal structure or debris, it is preferred to confine the controlled release dosage form units in a mesh-like bag within the drip chamber or other formulation chamber such as the mesh sleeve 51 shown in FIG. 11. In FIG. 11 there is also shown a plurality of controlled release dosage form units which may be employed in order to provide additional beneficial ingredients that are dispersible in the medium of the liquid enteral nutritional product in order to obtain a tailor-made nutrient composition for the patient. This may be especially helpful wherein none of the controlled release dosage forms at hand may have the exact combination of ingredients that is desired or needed for a patient, and the combination can be made up a la carte if there are at hand controlled release dosage form units containing the various ingredient contents desired.

Figure 12:
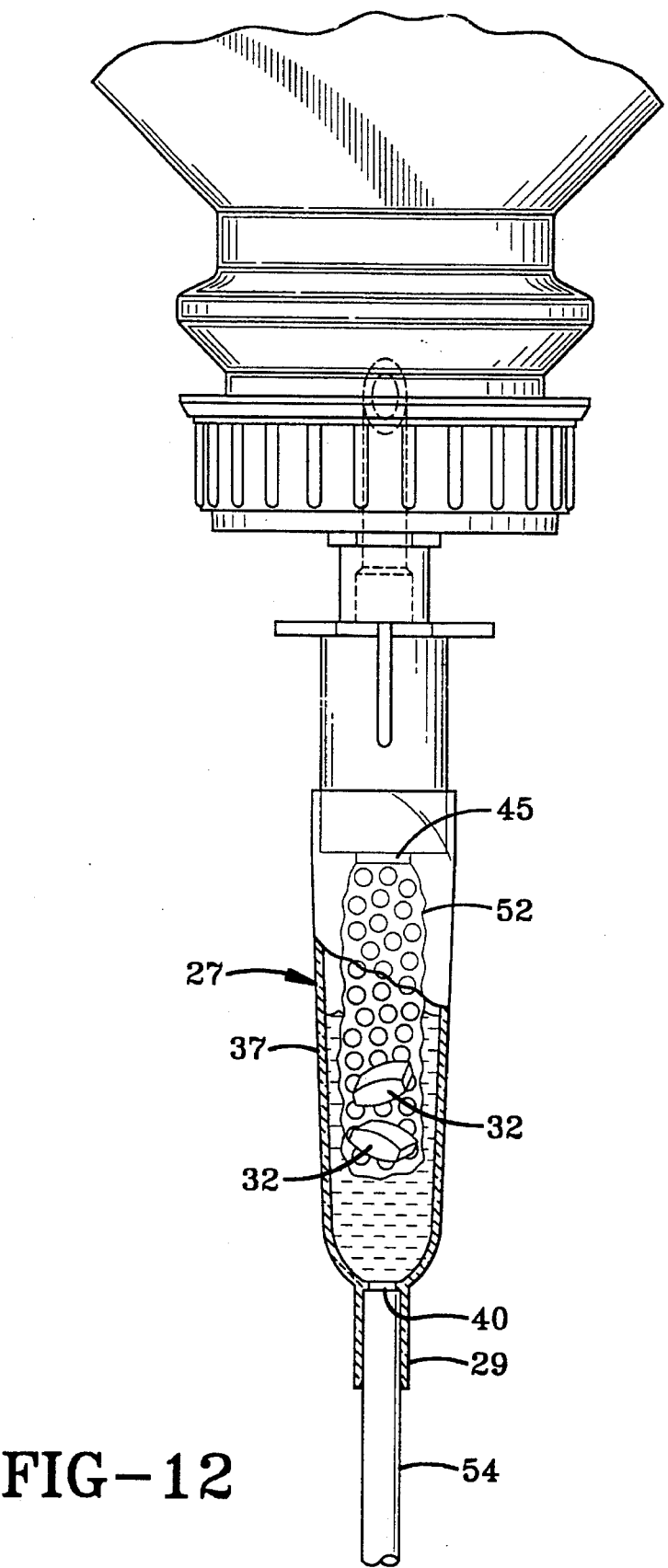
FIG. 12 is a view similar to FIG. 4, but with the controlled release dosage forms of any of FIGS. 7 to 9A confined within a foraminated, pierced, or fibrous sleeve or bag.

As seen is FIG. 12, a foraminous sleeve, or bag, that is, one with numerous holes in it, may be used to position the controlled release reservoir(s) in the drip chamber or other formulation chamber.

Figures 13, 13A:
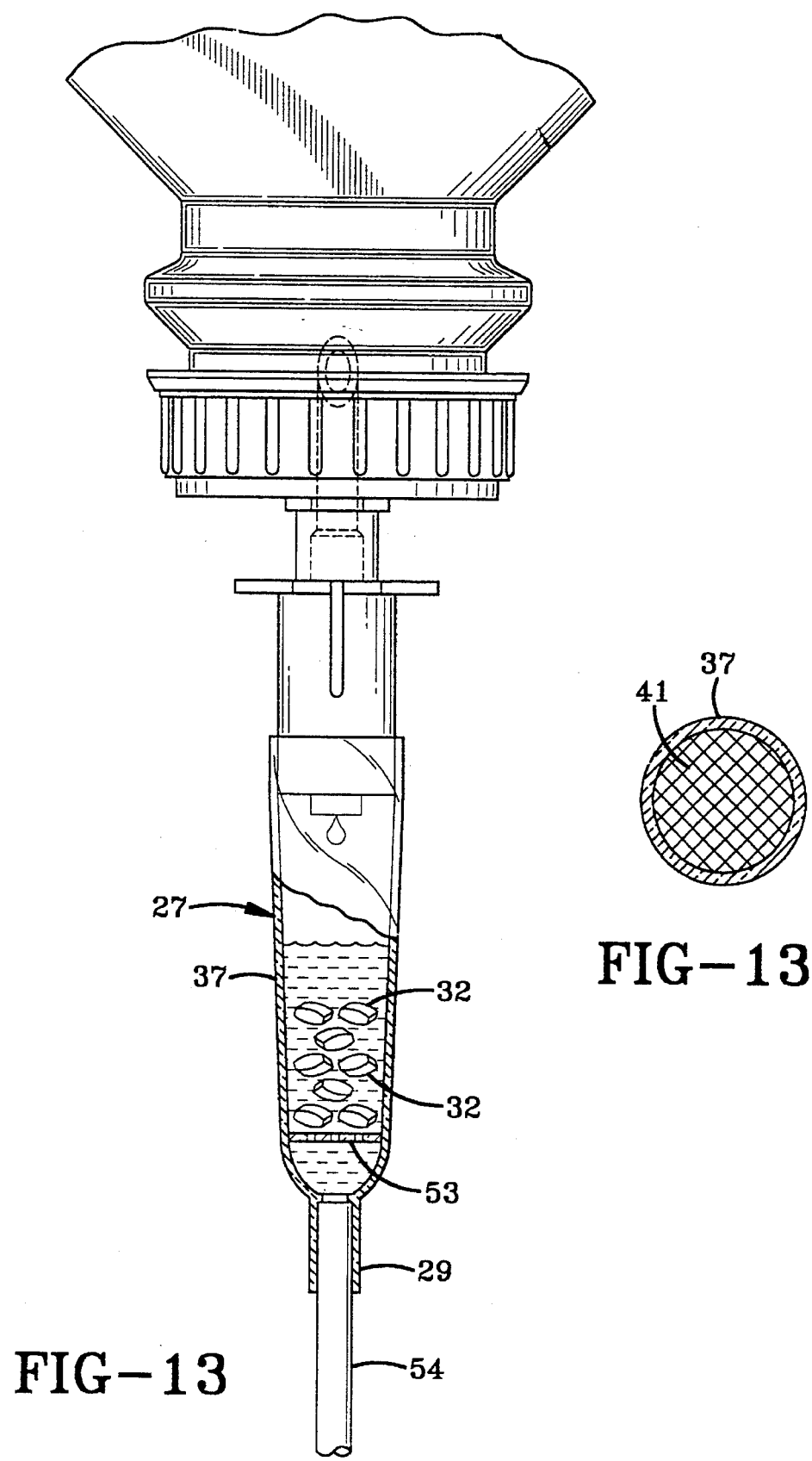
FIG. 13 is a view similar to FIG. 4, but with a plurality of the controlled release dosage forms of any of FIGS. 7 to 9A supported by a foraminous plate above the bottom orifice of the drip chamber.
FIG. 13A is a view in transverse section of a formulation chamber taken at the level just above a grid that has been placed in the drip chamber of FIG. 13 in place of the foraminous plate there shown for the support of a controlled release dosage form positioned in the drip chamber.

Or, turning now to FIG. 13, a plastic or ceramic or corrosion resistant metal plate 53 that is foraminous or pierced may be placed within the body of the lower part of the drip chamber 37, or other formulation chamber, to support the controlled release dosage form units, in this case, a very large number where the desired ingredient is needed in relatively large amount. If desired, the foraminous plate 53 may be replaced by a grid or screen 41, such as that shown in FIG. 13A and is also preferably formed of a plastic or vitrified ceramic or corrosion resistant metal, such as stainless steel.

The foregoing means of disposing, i.e., supporting, the controlled release dosage form units within the drip chamber may also be used in any additional formulation chambers in the feeding set employed.

Figure 7:
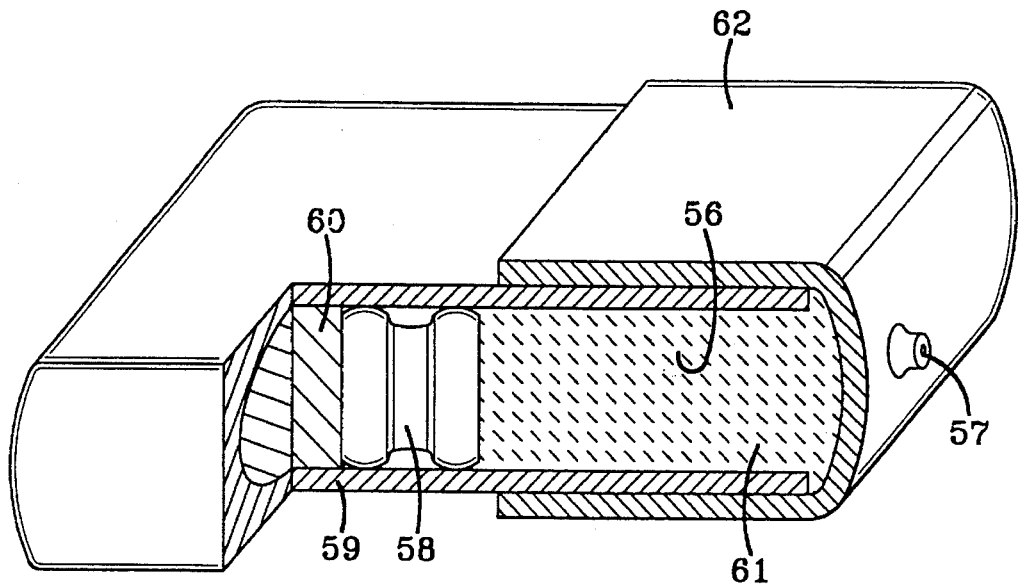
FIG. 7 is a perspective view, partly broken away and in section, of a rectangular solid-shaped controlled release dosage form, of the osmotic pump type, used to supply a beneficial ingredient or mixture thereof within the formulation chamber according to the invention.

The controlled release dosage form unit depicted in FIG. 7 is of the osmotic pump type that functions in the manner of the osmotically driven delivery device described and claimed in U.S. Pat. No. 5,318,558, the specification and drawings of which are incorporated herein by reference with respect to the structure of the controlled release dosage form units therein described and the method of making them and their mode of functioning, albeit here with different environments and contents and end uses. In the pump type controlled release dosage form units, or delivery devices, the beneficial ingredient(s) in liquid form, i.e., either in the liquid state or in solution in a suitable solvent, is expressed out from a cylindrical enclosure or cavity 56 within the reservoir through a small orifice 57 by the action of a piston 58 driven by pressure developed by osmotic infusion of moisture through a semi-permeable membrane 59 confining a hydro-active substance 60 behind the piston 58, driving the piston steadily toward the side of the reservoir where the ingredient(s) 61 is forced out through the orifice 57. Orifice 57 is very small and is preferably drilled by a laser beam. The cylindrical enclosure 56 is formed within an outer non-permeable membrane or coating 62. The hydro-active substance 60 may be a water-soluble salt like magnesium sulfate, magnesium chloride, potassium sulfate, sodium chloride, sorbitol, inositol, urea, or a saccharide such as glucose or fructose or dextran, or, a hydrophilic polymer such as a poly(hydroxyalkyl methacrylate) with a molecular weight of 30,000 to 5,000,000, or a poly(vinylpyrrolidine) with a molecular weight of 10,000 to 360,000, an anionic or cationic hydrogel or polyvinyl alcohol having low acetate residual.

Figure 8:
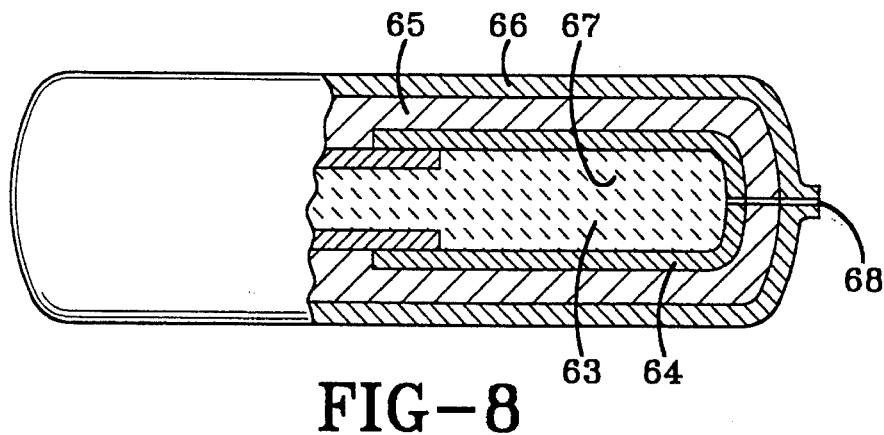
FIG. 8 is a view in front elevation, partly broken away and in section, of a nearly rectangular solid-shaped controlled release dosage form, of another osmotic device type, used to supply a beneficial ingredient or mixture thereof within the formulation chamber according to the invention.

The controlled release reservoir depicted in FIG. 8 is another osmotic dosage system with a sustained release dosage form that functions in the manner of the osmotically operated delivery device described and claimed in U.S. Pat. No. 5,324,280, the specification and drawings of which are hereby incorporated herein by reference with respect to the structure of the sustained release dosage form units there described and the method of making them and their mode of functioning, albeit here with different environments and contents and end uses. In this type of system, the beneficial ingredient(s) 63 to be fed in liquid state or solution form, is enclosed within a non-permeable coating 64 that is surrounded by a layer 65 of hydro-active material that is entirely confined within an outer semi-permeable membrane coating 66. Osmotic pressure developing in the hydro-active layer 65 upon infusion of moisture thereinto compresses the core 67 containing the liquid form beneficial ingredient(s) 63 and forces that liquid out steadily through a very small passageway 68 from the core 67 to the exterior of the reservoir.

Figure 8A:
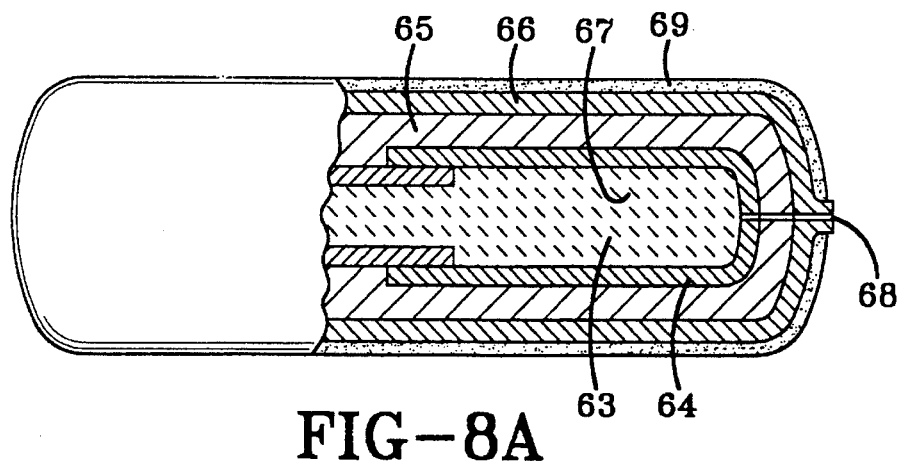
FIG. 8A is a view similar to FIG. 8 of a sustained release dosage form of the same type but with an external coating of marker dye that is readily taken up immediately in the medium of the liquid enteral nutritional product at the outset of commencing flow through the formulation chamber and of use wherein the dosage form contains marker dye for the sustained release thereof.

Turning now to FIG. 8A, the controlled release dosage form unit as shown in either of FIGS. 7 and 8 may be coated with a readily soluble coating, such as coating 69, which may be a coating of marker dye or beneficial agent for the purpose of getting a quick initial release of such dye or beneficial agent. In the case of a beneficial agent such as a medicament, this may be desirable in order to get a blood content level up quickly, after which a steady sustained release level may be needed.

Figure 9:
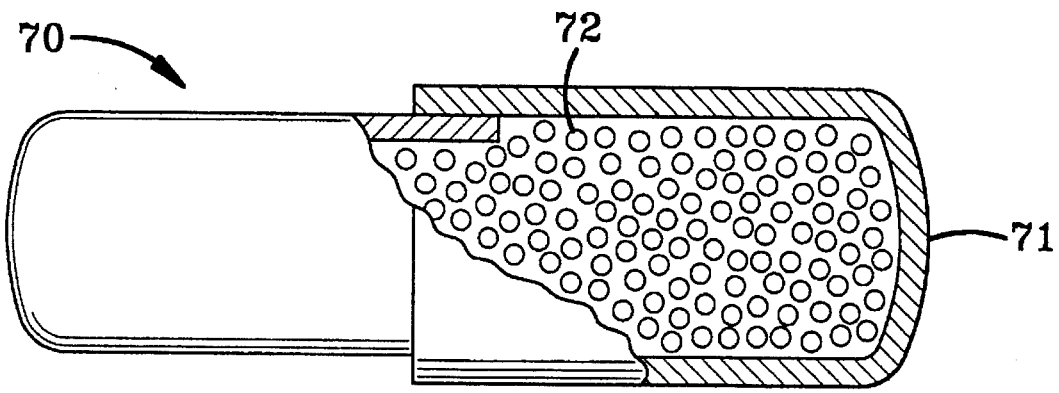
FIG. 9 is a view in front elevation, partly broken away and in section, of a nearly rectangular solid-shaped carrier of controlled release dosage forms, of the microencapsulated particle type or molecular sieving type, used to supply a beneficial ingredient or mixture thereof within the drip chamber according to the invention.

The controlled release reservoir 70 depicted in FIG. 9 is of the type in which there is provided, within a carrier envelope 71 that is very quickly soluble or disintegrable in the medium of the liquid enteral nutritional product, a quantity of microcapsules or molecular sieving type particles 72. If microcapsules, the particles 72 are microspheres each individually coated and each containing the same beneficial ingredient or mixture thereof, with a plurality of distinct numerical portions or fractions thereof each provided with a coating that dissolves or disintegrates in or is permeated by the medium of the liquid enteral nutritional product. The various numerical fractions, respectively, each have a coating of a different thickness whereby upon making a blend of the microcapsules with a fraction that is uncoated, the mixture shows a sustained release effect when exposed to an aqueous medium, such as the medium of a liquid enteral nutritional product. The envelope and coatings must essentially be acceptable for nutritional feeding, or disintegrable, i.e., suspendable, but not necessarily soluble.

If the particles 72 are of a molecular sieving type, or a mixture of two or more molecular sieving grades, the particles have been impregnated with a beneficial ingredient or ingredients to be supplied during feeding and the particles agglomerated into desired size granules or clumps that are usable with or without being coated, to form a controlled release dosage form usable according to the invention, the coating, if applied, being soluble, or disintegrable, i.e., suspendable, in or permeable to the medium of the liquid enteral nutritional product to be modified. The molecular sieving type material has a porous structure with non-aligned pores where pore size is critically controlled in manufacture in order to create the property of holding molecules of different size characteristics or molecular weights in a selective manner. The holding or storing properties impart sustained release behavior.

The carrier for controlled release dosage form units may also take the form shown in FIG. 9 but containing a fibrous material in which the fibers are hollow and permeable and slowly release substances such as the beneficial ingredients herein added to a nutritional product. A measured quantity of such fibers, in a coil or in chopped form, may be used in a retaining means such as a sleeve or bag, or agglomerated with a binder, or coated with a dispersible, disintegrable or permeable coating. Such fibers, which may be formed primarily of a cellulose ether or ester, are capable of storing up and subsequently yielding up a beneficial ingredient or mixture of ingredients, upon contact with flowing liquid enteral nutritional product within the drip chamber or other formulation chamber.

Figure 9A:
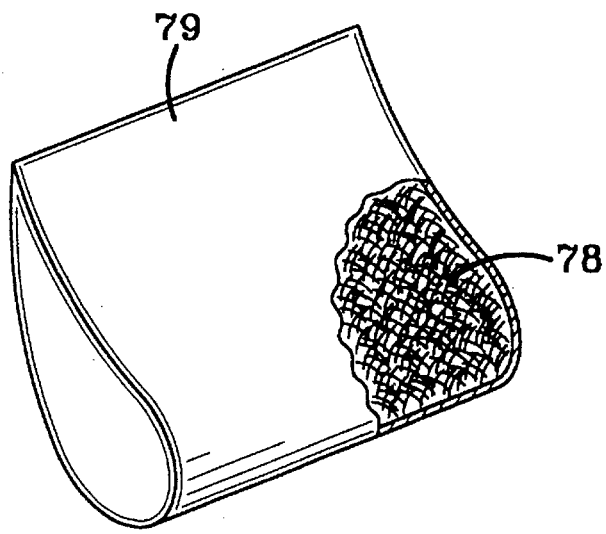
FIG. 9A is a perspective view, partly broken away and in section, of a highly permeable fibrous packet, preferably of the non-woven tea bag-type of carrier, suitable for placing in a drip chamber, or other formulation chamber, and capable of holding a sustained release dosage form, such as a coated tablet, or an osmotic delivery device, or a coated capsule, or a capsule containing a quantity of controlled release dosage forms in the form of microencapsulated particles or molecular sieving type material or permeable hollow fibers, each such dosage form article or unit containing at least one beneficial agent or a mixture thereof with marker dye. A beneficial agent not in controlled release dosage form, whether tabletted or agglomerated or loose particulate, also may be placed in measured amount in a porous carrier such as one or more fibrous packets of the sort shown in FIG. 9A and used in a formulation chamber in addition to one or more controlled release dosage form units or separately if there is at least one such controlled release dosage form placed in the same formulation chamber or in at least one formulation chamber used with the same communication means. A small quantity of marker dye not in controlled release dosage form may also be placed in the fibrous packet for quick initial dye marking.

The fibrous and highly porous tea bag-type of carrier envelope 79 shown in FIG. 9A may also be used to hold or support, within a formulation chamber, a quantity of microencapsulated microspheres, or a quantity of molecular sieving type material or, for example, a quantity of chopped fine hollow permeable fibers 78, any of which forms holding or containing a dosage amount of one or more beneficial agents. Such a tea bag-type of envelope, or a plurality thereof, may also be used to position within a formulation chamber any combination of: (1) one or more beneficial agents in controlled release dosage form; (2) one or more beneficial agents in controlled dosage form along with one or more beneficial agents not in controlled dosage form, wherein the beneficial agents not in controlled dosage form may be the same or different agents than those present in controlled dosage form; and (3) a marker dye or dye mixture in combination with either (1) or (2) and in a controlled release dosage form setting, as well as in any external coatings of controlled release dosage form units. Wherein more than one formulation chamber is used, the additional formulation chamber may have positioned therein, e.g., a fibrous carrier bag having therein only non-controlled beneficial agent along with or without marker dye.

Any mode of making a sustained or controlled release storage coating, envelope or binder may be used in making a controlled release dosage form unit usable according to the invention so long as the soluble, dispersible or disintegrable components of the dosage form units used are physiologically acceptable and the controlled release dosage form unit is capable of storing one or more beneficial ingredients as above defined until use and releasing the same into a liquid enteral nutritional product at a useful rate or manner and/or over a useful period of time of at least one-half hour and preferably over at least two hours during enteral feeding, or longer if needed for certain medicaments and nutrients. Tablets and capsules and other dosage forms may generally be coated with well known materials that slow down and delay the solubilization or suspension of the beneficial agent, materials such as zein, shellac, methacrylate polymers and copolymers, and cellulose ethers and esters that are frequently used for the purpose. Such materials are described in U.S. Pat. No. 5,160,742 and are generally adaptable for the present purpose, although the coated articles described in the patent are used in a different manner.

Wherein it is necessary or quite important to provide a beneficial ingredient, or a mixture of ingredients, as herein defined, for example, one or more medicaments, according to the invention and at a fairly uniform rate over time, with preferably not more than about a 25% variation above or below the median rate over a period of two to about 24 hours or more, the osmotic pump and other osmotic delivery systems are to be preferred. Generally, a wide range of rates is usable as long as at least an effective amount is supplied without reaching excessive amounts.

Amongst the beneficial agents that are most likely to be added to conventional enteral nutritional compositions are, for example, nutrients, such as, glutamine, arginine, fermentable dietary fibers, non-fermentable dietary fibers, enzymes such as lipases, combinations of amino acids, oligosaccharides such as fructo-oligosaccharides, vitamins, short chain ($C_3$–$C_4$) fatty acids, pyruvate precursors in the form of pyruvamide, or pyruvyl-amino acids, such as, pyruvylglycine, pyruvyl-alanine, pyruvyl-leucine, pyruvyl-valine, pyruvyl-sarcosamine and their amides, esters and salts, structured lipids, d-cyroinositol, lactoferrin, marine oils and acidulents such as ascorbic acid. An example of a structured lipid which provides excellent nutritional support is a glycerol backbone with at least one gamma linolenic acid or dihomogamma-linolenic acid residue in combination with a medium chain ($C_6$–$C_{12}$) fatty acid residue and a $C_{18}$–$C_{22}$ n-3 fatty acid residue selected from alpha-linolenic and stearodonic, eicosapentaenoic and docosahexaenoic acid.

Medicaments that may usefully administered in this manner include, for example, antihistamine drugs; anti-infective agents, such as antibiotics, antivirals and urinary tract anti-infectives; antineoplastic agents; autonomic drugs such as adrenergic agents and skeletal muscle relaxants; blood formation and coagulation drugs; cardiovascular drugs; central nervous system agents; diagnostic agents; electrolytic, caloric and water balance agents; enzymes; antitussive, expectorant and mucolytic agents; gastrointestinal drugs such as antacids; gold compounds; hormones and synthetic substitutes; smooth muscle relaxants; and unclassified therapeutic agents. Other examples are $H_2$ blockers like Tagamet®, prokinetic medications, bioactive peptides, medication for diabetic condition, chemotherapy agents, or any medication intended for oral administration that will not react adversely with the nutritional formulation being fed into the gastrointestinal tract.

Probiotics that may be usefully administered in this manner include, for example, *Lactobacillus acidophilus* GG, as described in U.S. Pat. 4,839,281, *Lactobacillus reuteri*, *Lactobacillus animalis*, and *Lactobacillus salivarius*, as described in WO 93/02558. Probiotics are live microorganisms that aid in the digestion of food or that help control the population of harmful microorganisms in the intestines.

If desired, a physiologically acceptable marker dye or dye mixture may be provided in the formulation chamber or chambers in addition to one or more of the beneficial ingredients above disclosed in order that the flow of modified liquid nutritional product may be made visible as an aid to the caregiver. This may be done by placing in the formulation chamber one or more sustained release dosage form units containing both the dye or dye mixture and the beneficial ingredient(s), if such dosage form units are available. Or, a controlled release dosage form unit containing the dye or dye mixture and a separate controlled release dosage form unit containing the beneficial ingredient(s) may be placed together in the formulation chamber. As indicated above, in order to impart prompt visibility to the flow of modified nutritional product as an aid to the caregiver, it may be preferred to apply an external, readily soluble coating of the marker dye to a controlled release dosage form unit, ordinarily one containing marker dye. The marker dye is admixed with a small amount of one or more conventional easily dispersible tablet coating excipients, such as, polyvinylpyrrolidine having an average molecular weight in the range of about 35,000 to 50,000, mannitol, magnesium stearate, and zein or guar gum, in applying the dye to the dosage form unit during manufacture. Generally the amount of excipients in total is less than about 10 percent by weight of the coating. Or, the dosage form unit may be simply dipped in a solution of the marker dye and dried.

A marker dye or dye mixture that is useful according to the invention is a colorant dye or a fluorescent dye or a mixture of such dyes that is physiologically acceptable to the patient and compatible with the beneficial agents being fed therewith. The dye or dye mixture must also be capable of being taken up in detectable concentration in the liquid medium of the liquid enteral nutritional product while the product flows through a drip chamber or other formulation chamber having positioned therein at least one sustained release dosage form unit containing the marker dye or dyes. If the dye is detectable in the drip chamber, it can be expected to be detectable, ordinarily, if it somehow reaches the oral cavity of the patient.

The marker dye employed may be a colorant dye that imparts color that is visible under white light, for example, normal daylight or artificial room light encountered in a hospital or clinic, or, the marker dye may be a fluorescing dye that fluoresces visibly under ultraviolet light, or, a mixture of a colorant dye and a fluorescing dye. A mixture of a colorant dye and a fluorescing dye appears to be especially advantageous in that flow through the formulation chamber is readily perceived under normal lighting conditions with colorant dye present, while even a small amount of nutritional product out of place, for example, in the oral cavity or nasal passage, will be more easily detected with the aid of ultraviolet light if it contains a fluorescing dye. This is because of the nature of the fluorescing dyes that are especially visible under ultraviolet light even when present in very low concentration.

The dye or dye mixture used must be physiologically acceptable. Usually food grade colorant dyes approved under the provisions of the United States Food, Drug and Cosmetic Act are suitable. Preferred are F.D. & C. Blue #1 and F.D. a C. Blue #2 dyes. The dye or dye mixture used must be soluble in the medium of the liquid enteral nutritional product being fed and compatible with the beneficial ingredient(s) being added during the feeding. Generally about 0.1 milligram of dye per milliliter of liquid enteral nutritional product is desired to give a readily visible coloration to the nutritional product.

Wherein it is important to be able to detect misdirected liquid enteral nutritional product, the marker dye used may be a fluorescing dye, such as F.D.& C. Red #3, which is highly visible at a very low concentration under ultraviolet light and also imparts a visible coloration to the liquid nutritional product under white light conditions. Other suitable fluorescing dyes are: quinine, F.D.& C. Red #22, F.D.& C. #28, fluorescein, and D 282 UV Blue available from DaGlo of Cincinnati, Ohio and also identified as 16470-24-9 in the Chemical Abstracts System with a color index of 220 as a fluorescent brightener. As indicated above, if desired, a mixture of colorant dye and fluorescing dye may be used. Generally, adding to the nutritional product in the formulation chamber about 0.01 to 0.05 mg/ml of fluorescing dye is adequate for detectability under ultraviolet light.

A feeding set, such as the kit 20 shown in FIG. 15, is conveniently provided in packaged form ready for use in feeding a liquid enteral nutritional product. The kit includes a Controlled release dosage form unit 32, a drip chamber 27 or other formulation chamber, and liquid communication means 28 consisting mainly of a length of flexible tubing attached at one end to the outlet of the drip chamber 27 and at the other end to a fitting 30 for coupling attachment to a feeding tube. The fitting 30 is shown with a cap 55 telescoped for purposes of illustration. The cap is simply for protection of the fitting 30 until the feeding set is used. The controlled release dosage form unit 32 has already been placed in the drip chamber 27 and contains one or more beneficial ingredients as defined hereinabove for modification of a liquid enteral nutritional product during feeding thereof, and additionally a marker dye, if desired. The kit may also be provided with a plurality of controlled release dosage form units 32 within the drip chamber 27 if a single dosage form unit does not contain each type of beneficial ingredient desired for modification of the nutritional product or if it is desired to add a marker dye and it is not present in the controlled release dosage form units for the beneficial ingredients selected.

Figure 10:
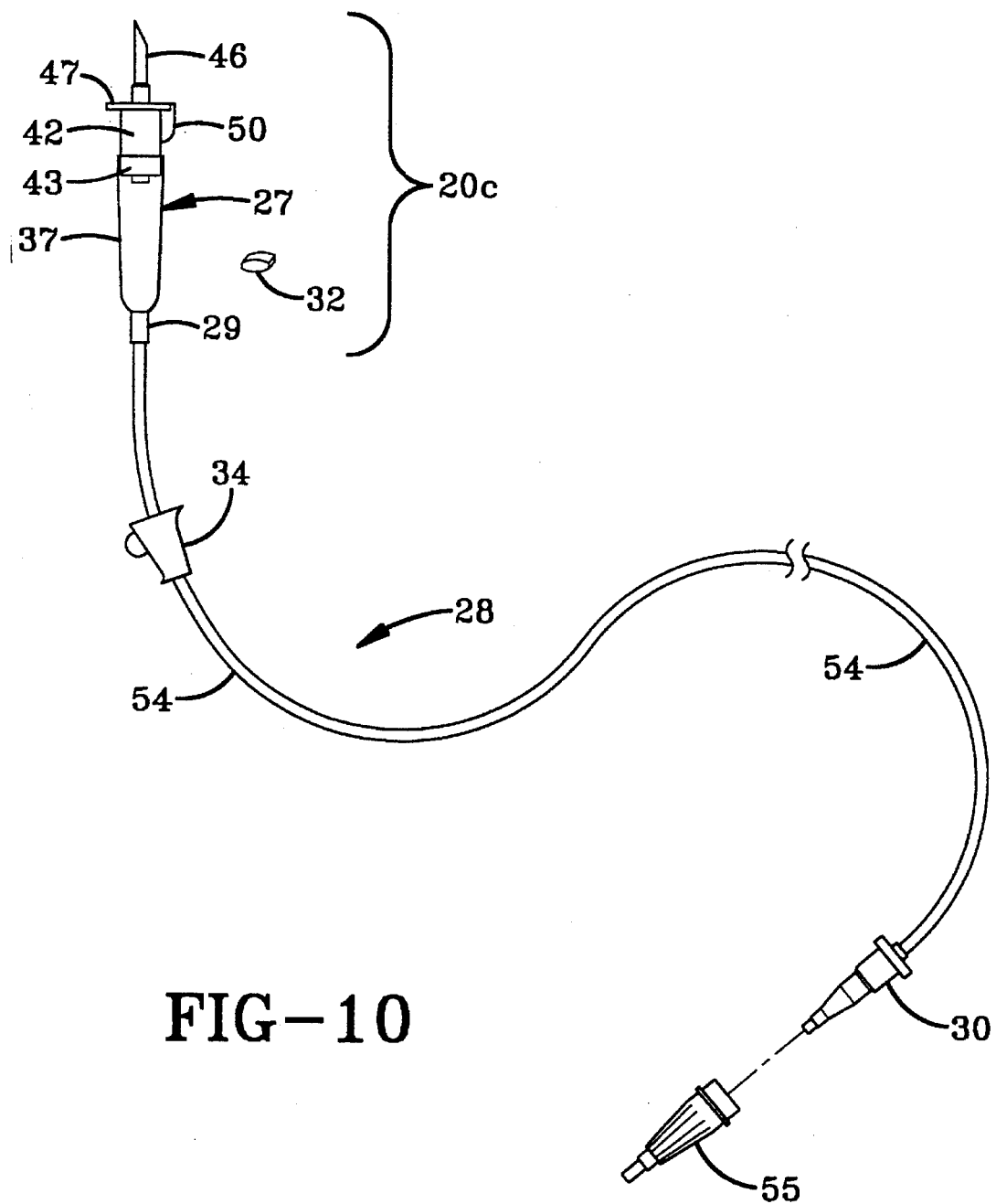
FIG. 10 is a view in side elevation and partly truncated, of a feeding set, or kit, including a beneficial agent in controlled release dosage form to be placed in the formulation chamber by the caregiver, the kit being useful in modifying a liquid enteral nutritional composition during the feeding thereof according to the invention.

A similar kit 20c, as shown in FIG. 10, includes the controlled release dosage form unit 32 which has not been placed in the drip chamber 27 before shipping the kit, but accompanies the drip chamber as part of the kit. Other kits are prepared with various numbers and varieties of controlled release dosage form units containing various beneficial agent and marker dye combinations and beneficial agents not in controlled release form, to accompany the feeding sets.

In a preferred embodiment of the apparatus of the invention of the type illustrated in FIG. 2, a controlled release dosage form unit of the type illustrated in FIG. 8A is positioned in the formulation chamber. The dosage form unit contains glutamine and F.D.& C. Blue #1 dye and is coated with a layer of the same blue dye admixed with about 3 percent by weight in total of polyvinylpyrrolidine having an average molecular weight in the range of about 35,000 to 44,500. The feeding kit is connected to a hanging supply container of a liquid enteral nutritional product having a viscosity of about 40 cps., such as PULMOCARE®, a product of the Ross Products Division of Abbott Laboratories, Columbus, Ohio, and a steady flow of the nutritional product is commenced. The dye coating provides immediate visible color within the drip chamber within 2 seconds and the controlled release dosage form unit provides the blue dye in a concentration of at least 0.075 mg/ml for a period of over 1,440 minutes during the flow of about 3,000 ml of the liquid enteral nutritional product. The dosage form unit also provides glutamine at a concentration of at least 1.25 mg/ml during the flow of the liquid enteral nutritional product, commencing after about 1 ml of flow.

We claim:

1. An apparatus for modifying a liquid enteral nutritional product during the feeding thereof comprising:

a formulation chamber, the formulation chamber having an inlet and an outlet and the inlet connected to a container with a liquid enteral nutritional product having a viscosity in the range of about 5 to about 300 centipoises so as to receive said product therefrom, the formulation chamber further comprising at least one beneficial agent in at least one controlled release dosage form unit and the formulation chamber containing the at least one controlled release dosage form unit, each beneficial agent being selected from the group consisting of nutrients, medicaments, probiotics and diagnostic agents that are each dispersed in said liquid enteral nutritional product, the controlled release dosage form unit being capable of delivering each beneficial agent into said liquid enteral nutritional product over a time period in the range of at least about 30 minutes during the feeding thereof to a patient.

2. The apparatus of claim 1 wherein the formulation chamber is a drip chamber.

3. The apparatus of either claim 1 or claim 2 wherein the formulation chamber comprises additionally at least one beneficial agent not in a controlled release dosage form.

4. The apparatus of either claim 1 or claim 2 wherein the formulation chamber comprises additionally at least one marker dye in a controlled release dosage form unit, said controlled release dosage form unit being a means for providing and dispensing marker dye into a liquid enteral nutritional product having a viscosity in the range of about 5 to about 300 centipoises when the controlled release dosage form unit is physically contacted thereby during the feeding thereof to a patient over a time period of about 2 to about 24 hours.

5. The apparatus of claim 4 wherein the controlled release dosage form unit containing marker dye is coated with a quick release layer of marker dye.

6. The apparatus of either claim 1 or claim 2 wherein the formulation chamber comprises additionally both a marker dye in a controlled release dosage form unit and at least one beneficial agent not in a controlled release dosage form unit, said controlled release dosage form unit being a means for dispensing marker dye into a liquid enteral nutritional product having a viscosity in the range of about 5 to about 300 centipoises when the controlled release dosage form unit is physically contacted thereby during the feeding thereof to a patient over a time period of about 2 to about 24 hours.

7. The apparatus of claim 2 wherein the drip chamber has in fluid connection to the outlet thereof at least one formulation chamber, and at least one of the drip chamber and each such formulation chamber comprising at least one beneficial agent in a controlled release dosage form unit and the other chamber or chambers comprising at least one member of the group consisting of (a) beneficial agents in controlled release dosage form units, (b) beneficial agents not in controlled release dosage form, and (c) marker dyes in controlled release dosage form units wherein said controlled release dosage form is a means for dispensing marker dye into a liquid enteral nutritional product having a viscosity in the range of about 5 to about 300 centipoises when the controlled release dosage form unit is physically contacted thereby during the feeding thereof to a patient over a time period of about 2 to about 24 hours.

8. The apparatus of claim 1 wherein the outlet of the formulation chamber is connected to fluid communication means connectable to a feeding tube which communicates with the gastrointestinal tract of a patient.

9. The apparatus of claim 1 wherein the at least one beneficial agent is glutamine.

10. The apparatus of claim 1 wherein the at least one beneficial agent is a probiotic.

11. The apparatus of claim 1 wherein the at least one beneficial agent is a pyruvate precursor.

12. The apparatus of claim 1 wherein the at least one beneficial agent is a structured lipid.

13. An apparatus for liquid enteral nutritional product feeding comprising:

a formulation chamber having an inlet and an outlet and connected to a supply container with a liquid enteral nutritional product having a viscosity in the range of about 5 to 300 centipoises so as to receive said product therefrom, the formulation chamber further comprising at least one beneficial agent in controlled release dosage form unit, each beneficial agent in controlled release dosage form unit being disposed within the formulation chamber so as to be wetted by or immersed in the liquid enteral nutritional product traversing therethrough and each beneficial agent being selected from the group consisting of: nutrients, medicaments, probiotics and diagnostic agents, and chemically and physiologically compatible combinations thereof, and, any of the foregoing beneficial agents or chemically and physiologically compatible combinations thereof together with a physiologically acceptable marker dye, each beneficial agent and marker dye disposed in the formulation chamber being dispersed in the medium of the liquid enteral nutritional product, the controlled release dosage form unit being capable of delivering each beneficial agent into said liquid enteral nutritional product over a time period of at least about 30 minutes; and fluid communication means capable of operatively connecting the outlet of the drip chamber to a tube for feeding, into the gastrointestinal tract of a patient, the modified liquid enteral nutritional product.

14. The apparatus of claim 13 wherein the formulation chamber is a drip chamber.

15. The apparatus of claim 13 wherein the formulation chamber comprises a plurality of controlled release dosage form units each containing the same or different at least one beneficial agent.

16. The apparatus of claim 13 for use in delivering an aqueous liquid enteral nutritional product, wherein said at least one beneficial agent is water soluble or dispersible and the controlled release dosage form unit is a water soluble or dispersible ingredient delivery device containing said at least one water soluble or dispersible beneficial agent, the device comprising;

at least one inner mass transfer conductor;

the at least one water soluble or dispersible beneficial agent being present in a physiologically useful or diagnostically detectable amount, with the at least one water soluble or dispersible beneficial agent disposed in the at least one inner mass transfer conductor, the at least one inner mass transfer conductor being permeable to the passage of the at least one water soluble or dispersible beneficial agent; and a membrane surrounding the at least one inner mass transfer conductor, which membrane releases at least a useful amount of the at least one water soluble or dispersible beneficial agent into the liquid enteral nutritional product employed when the product is gradually passed over the membrane and administered enterally to a patient.

17. The apparatus of claim 13 for use in delivering an aqueous liquid enteral nutritional product, wherein said at least one beneficial agent is water soluble or dispersible and the controlled release dosage form unit is an osmotically driven device, the device comprising:

a capsule formed by an exterior wall made up, at least in part, by a semipermeable composition that maintains its integrity in the presence of an aqueous fluid, the exterior wall surrounding a hydro-activated layer comprising a hydro-activated swellable composition or a hydro-activated composition that occupies space at a controlled rate, and an inner capsule surrounded by the hydro-activated layer and communicating with a lumen extending to the exterior of the outer capsule, the inner capsule containing at least a useful amount of the at least one water soluble or dispersible beneficial agent in liquid formulation form and the wall of the inner capsule being substantially non-permeable to the liquid enteral nutritional product.

18. The apparatus of claim 13 wherein the controlled release dosage form unit is a particulate controlled release composition comprising microencapsulated particles containing at least a useful amount of the at least one beneficial agent, the particles having a plurality of coating thicknesses that gradually dissolve or disintegrate and release the at least one beneficial agent within the particle when contacted over time by the liquid enteral nutritional product.

19. The apparatus of claim 13 wherein the controlled release dosage form unit is a molecular sieving type dosage form impregnated with at least a useful amount of the at least one beneficial agent, the molecular sieving dosage form gradually yielding up the at least one beneficial agent to the medium of the liquid enteral nutritional product when contacted over time by the liquid enteral nutritional product.

20. The apparatus of claim 13 wherein the controlled release dosage form unit contains as the beneficial agent at least one nutrient selected from the group consisting of glutamine, vitamins arginine, oligosaccharides, short chain fatty acids, enzymes, fermentable dietary fibers, non-fermentable dietary fibers, pyruvamide, pyruvyl-amino acids and their amides, esters and salts, structured lipids, d-cyroinositol, lactoferrin, marine oils and acidulants.

21. The apparatus of claim 20 wherein the controlled release dosage form unit contains as the beneficial agent at least one nutrient selected from the group consisting of glutamine, ascorbic acid and a pyruvate.

22. The apparatus of claim 13 wherein the controlled release dosage form unit contains as the beneficial agent at least one medicament selected from the group consisting of antacids, antibiotics, probiotic medications, prokinetic medications, bioactive peptides, medication for diabetic condition, chemotherapy agents, and any other medication intended for oral administration that will not react adversely with the nutritional formulation being fed into the gastrointestinal tract.

23. The apparatus of claim 13 wherein the controlled release dosage form unit contains as the beneficial agent a probiotic selected from the group consisting of *Lactobacillus reuteri Lactobacillus acidophilus, Lactobacillus animalis* and *Lactobacillus salivarius.*

24. The apparatus of claim 13 wherein the formulation chamber contains at least one beneficial agent selected from the group consisting of a marker dye in a controlled release dosage form unit and a beneficial agent not in controlled release dosage form unit in addition to the controlled release dosage form unit containing beneficial agent.

25. The apparatus of claim 13 wherein each controlled release dosage form unit contains a physiologically acceptable marker dye in addition to the at least one beneficial agent.

26. The apparatus of claim 13 wherein the controlled release dosage form unit is provided with an exterior layer that substantially maintains its integrity for at least the useful life of the dosage form unit during a feeding while exposed to liquid enteral nutritional composition, and the dosage form unit is in the shape of a rectangular solid.

27. The apparatus of claim 13 wherein the controlled release dosage form unit is confined within a mesh bag within the drip chamber.

28. The apparatus of claim 13 wherein the controlled release dosage form unit is confined within a foraminous bag within the drip chamber.

29. The apparatus of claim 13 wherein the fluid communication means includes a flexible tubing section suitable for use with a pump.

30. The apparatus of claim 13 wherein the drip chamber contains a plurality of controlled release dosage form units.

31. The apparatus of claim 13 wherein the fluid communication means includes additionally as a component thereof at least one additional formulation chamber having therein at least one controlled release dosage form unit containing the same or different at least one beneficial agent.

32. The apparatus of claim 31 wherein at least one of the drip chamber and at least one additional formulation chamber contains a plurality of controlled release dosage form units containing at least one beneficial agent.

33. The apparatus of claim 31 wherein the at least one additional formulation chamber contains a controlled release dosage form unit containing only a physiologically acceptable marker dye.

34. A drip chamber adapted for use as part of an enteral feeding set, the drip chamber comprising a sustained release dosage form unit, and a liquid enteral nutritional product having a viscosity in the range of about 5 to about 30 centipoises, the sustained release dosage form unit being disposed within the drip chamber and containing at least a useful amount of at least one beneficial agent for modification of said liquid enteral nutritional product during feeding, the beneficial agent being selected from the group consisting of nutrients, medicaments, probiotics and diagnostic agents, and chemically and physiologically compatible combinations thereof, and any of the foregoing beneficial agents or combinations of beneficial agents together with a physiologically acceptable marker dye or mixture of dyes, the controlled release dosage form unit being a means of delivering each beneficial agent into said liquid enteral nutritional product over a time period of at least about 30 minutes.

35. The drip chamber of claim 34 having disposed therein at least one additional sustained release dosage form unit, each unit containing at least a useful amount of at least one of the beneficial agents.

36. A kit for feeding liquid enteral nutritional product into the gastrointestinal tract of a patient, comprising:

a formulation chamber having an inlet and an outlet and connected to a supply container with a liquid enteral nutritional product having a viscosity in the range of about 5 to about 300 centipoises so as to receive said product therefrom;

the formulation chamber further comprising at least one controlled release dosage form unit containing at least one beneficial agent and up to a plurality of marker dyes, each at least one controlled release dosage form unit being disposed within the formulation chamber so as to be wetted by or immersed in said liquid enteral nutritional product within said formulation chamber; and fluid communication means having first and second ends, the first end being operatively connected to the outlet of the formulation chamber and the second end being capable of being operatively connected to a tube for feeding a liquid enteral nutritional product into the gastrointestinal tract of a patient, each controlled release dosage form unit being a means of delivering each beneficial agent into said liquid enteral nutritional product over a time period of at least about 30 minutes.

37. A kit for feeding liquid enteral nutritional product into the gastrointestinal tract of a patient, comprising:

a formulation chamber having an inlet and an outlet and connected to a supply container with a liquid enteral nutritional product having a viscosity in the range of about 5 to about 300 centipoises so as to receive said product therefrom;

at least one controlled release dosage form unit containing at least one beneficial agent and up to a plurality of marker dyes, each at least one controlled release dosage form unit accompanying the formulation chamber and being outside thereof; and fluid communication means having first and second ends, the first end being operatively connected to the outlet of the formulation chamber and the second end being capable of being operatively connected to a tube for feeding a liquid enteral nutritional product into the gastrointestinal tract of a patient, each controlled release dosage form unit being capable of delivering each beneficial agent into said liquid enteral nutritional product over a time period of at least about 30 minutes.

* * * * *

UNITED STATES PATENT AND TRADEMARK OFFICE
CERTIFICATE OF CORRECTION

PATENT NO. : 5,531,681
DATED : July 2, 1996
INVENTOR(S) : Walton, et. Al.

It is certified that error appears in the above-indentified patent and that said Letters Patent is hereby corrected as shown below:

Column 21, line 50, change "the medium of the" to --said--.
Column 22, line 57, change "vitamins arganine" to --vitamins, arganine--.

Signed and Sealed this

Tenth Day of June, 1997

Attest:

BRUCE LEHMAN

Attesting Officer

Commissioner of Patents and Trademarks